United States Patent [19]

Murad et al.

[11] Patent Number: 5,380,945
[45] Date of Patent: Jan. 10, 1995

[54] GUANIDINO COMPOUNDS AS REGULATORS OF NITRIC OXIDE SYNTHASE

[75] Inventors: Ferid Murad, Lake Forest; James F. Kerwin, Grayslake; Lee D. Gorsky, Highland Park, all of Ill.

[73] Assignee: Abbott Laboratories, Abbott Park, Ill.

[21] Appl. No.: 159,972

[22] Filed: Nov. 30, 1993

Related U.S. Application Data

[63] Continuation-in-part of Ser. No. 755,398, Sep. 5, 1991, Pat. No. 5,288,897, which is a continuation-in-part of Ser. No. 369,364, Jun. 21, 1989, abandoned.

[51] Int. Cl.$^6$ .................... C07C 249/00; A01N 37/52
[52] U.S. Cl. .................... 564/108; 564/104; 564/226; 564/227; 564/229; 514/634
[58] Field of Search ............... 564/108, 104, 226, 227, 564/229; 514/634

[56] References Cited

U.S. PATENT DOCUMENTS 4,677,226  6/1987  Lutz et al. ................ 564/108
5,296,498  3/1994  Molen et al. .............. 514/401

Primary Examiner—Raymond J. Henley, III
Assistant Examiner—Keith MacMillan
Attorney, Agent, or Firm—Richard A. Elder; James D. McNeil; Edward H. Gorman, Jr.

[57] ABSTRACT

Compounds of the formula:

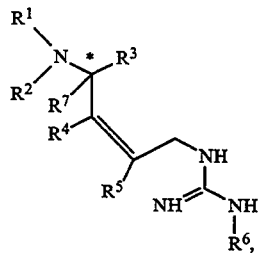

useful as regulators of nitric oxide synthase that indirectly modulate cyclic guanosine monophosphate (cGMP), pharmaceutical compositions thereof, for treating disorders of vascular smooth muscles, macrophages, neurons, platelets, bronchial smooth muscles, optic muscles and gastrointestinal smooth muscles, sickle cell anemia and diabetes.

6 Claims, No Drawings

GUANIDINO COMPOUNDS AS REGULATORS OF NITRIC OXIDE SYNTHASE

CROSS REFERENCE TO RELATED APPLICATIONS

This application is a continuation-in-part U.S. patent application Ser. No. 07/755,398, filed Sep. 5, 1991 now U.S. Pat. No. 5,288,897, which is a continuation-in-part of U.S. patent application Ser. No. 07/369,364, filed Jun. 21, 1989, now abandoned.

TECHNICAL FIELD

The present invention relates to novel unsaturated guanidino compounds, to compositions thereof useful in regulating the production of soluble guanylate cyclase or nitric oxide, to intermediates useful in the production thereof, and to a method of treating disorders of the vascular system or diseases of the cartilage, including hypotension, hypertension, coronary vasospasm, cerebral vasoconstriction, cardiomyopathy, atherogenesis, atherosclerosis, myocardial ischemia, cerebral ischemia, diabetes, endotoxemia, sepsis, asthma and rhinitis. synovitis, chondroarthritis and osteoarthritis.

BACKGROUND OF THE INVENTION

Furchgott (Nature, 1980, 288:373–6) reported in 1980 that endothelial cells release a powerful vasodilator which is termed endothelium-derived relaxing factor (EDRF). Subsequent research has shown that many endothelium-dependent receptor agonists, including, for example, adenosine diphosphate (ADP), adenosine triphosphate (ATP), 5-hydroxytryptamine (5-HT), thrombin, acetylcholine (ACh), vasoactive intestinal polypeptide (VIP), oxytocin, cholecystokinin (CCK), calcitonin gene-related peptide, noradrenaline, histamine, calcium ionophores, melittin and ergometrine invoke the release of EDRF. The release of EDRF, in turn, stimulates the soluble form of the enzyme guanylate cyclase, thereby increasing levels of the second messenger, cyclic guanosine monophosphate (cGMP), which, in turn, produces vasorelaxation. Reviews are available which discuss this process in more detail (see, for example, A. M. Katz, *J. Am. Coll. Cardiol.*, 1988, 12: 797–806; J. A. Angus and T. M. Cocks, *Pharmaceutical Therapeutics*, 1989, 41: 303–52; S. A. Waldman and F. Murad. *Pharmacological Reviews*, 1987, 39: 163–196; F. Murad, *J. Clin. Invest.*, 1986, 78: 1–5; L. J. Ignarro, *Biochem. Pharmacol.*, 1991, 41: 485–90; and S. Moncada, R. M. J. Palmer and E. A. Higgs, *Pharmacological Reviews*, 1991, 43: 109–142).

Pharmacological characterization of EDRF and its effects has been an active area of research over the past eleven years (K. Shikano et al., *J. Pharmacol. Exp. Therap.*, 1988, 247: 873–81 and L. J. Ignarro, *Annu. Rev. Pharmacol. Toxicol.*, 1990, 30: 535–60), and now there is substantial evidence that nitric oxide (NO) is the major endothelium-derived relaxing factor (R. M. J. Palmer et al, *Nature*, 1987, 327: 524–6; S. Moncada et al., *Biochem. Pharmacol.*, 1989, 38: 1709–15; and S. Moncada et al., *Hypertension*, 1989, 12: 365–72). In particular, nitric oxide (NO) was tested and found to elicit a potent and transient relaxation of bovine coronary artery accompanied by cGMP accumulation (C. A. Guetter et al, *J. Cyclic Nucleotide Res.*, 1979, 5: 211–24) and it was also shown to activate soluble guanylate cyclase and to elevate tissue cGMP levels.

Recent reports (H. H. H. W. Schmidt et al., *European J. Pharmacol.*, 1988, 154: 213–6 and S. Moncada et al., *Hypertension*, 1988, 12: 365–72) have suggested that L-arginine may be the endogenous source of EDRF (NO), and this hypothesis is further supported by the observation that EDRF (NO) production is inhibited by the simple arginine derivative, $N^G$-methylarginine (R. M. J. Palmer et al., *Biochem. Biophys. Res. Comm.*, 1988, 153: 1251–56; S. Moncada et al., *Biochemical Pharmacology*, 1988, 37: 2495–2501; and I. Sakuma et al., *Proc. Natl. Acad. Sci. USA*, 1988, 85: 8664–7).

Increasing evidence has been uncovered that suggests EDRF or EDRF-like substances may also control cGMP production in non-endothelial cells (J. Garthwaite, *Nature*, 1988, 336: 385–388 and T. J. Rimele et al., *J. Pharmacol. Exp. Therap.*, 1988, 245: 102–111) and that this method of guanylate cyclase regulation may be ubiquitous. A role in the regulation of neural transmission and a role in the neural control of gastrointestinal smooth muscle function has been elucidated (J. Collier and P. Vallance, *Trends in Pharmacological Sciences*, 1989, 428–31 and K. M. Desai et al., *Nature*, 1991, 351: 477–9). Compounds that control, inhibit, or otherwise regulate this pathway, therefore, have potentially many and varied therapeutic applications, for instance, as analgesics (Duarte et al., *European J. Pharmacology*, 1990, 186: 289–93), as cerebroprotectives (cf. Southham et al., *J. Neurochem.*, 1991, 56: 2072–81) and as hypocholesteremics (Cooke et al., *Circulation*, 1991, 83: 1057–62).

Recent work has shown that there are many isoforms of the EDRF (NO) synthase enzyme. The primary distinction among these isoforms is whether they are constitutive or inducible forms, but other factors which serve to distinguish these isoforms are their cellular localization and their cofactor requirements. Many of these isoforms have been arbitrarily given Roman numeral designations and are described in the table below, wherein NADPH represents reduced nicotinamide adenine dinucleotide phosphate, $BH_4$ represents tetrahydrobiopterin, FAD represents flavin adenine dinucleotide and FMN represents flavin mononucleotide.

| Type | Cosubstrates & Cofactors | Regulated by | $M_r$ of denatured protein* | Present in |
|---|---|---|---|---|
| I (soluble) | NADPH, $BH_4$ | $Ca^{++}$, calmodulin | 155 kDa** | brain and cerebellum |
| II (soluble) | NADPH, $BH_4$, FAD/FMN, thiols, $Mg^{++}$ | induced by endotoxin and cytokines | 125–135 kDa** | macrophages |
| III (particulate) | NADPH $BH_4$ | $Ca^{++}$, calmodulin | 135 kDa** | endothelial cells |

*Molecular weight determination by sodium dodecyl sulfate/polyacrylamide gel electrophoresis
**kiloDaltons Isoform I has been purified and characterized by Bredt and Snyder (*Proc. Natl. Acad. Sci. USA*, 1989, 87: 682–685) and by Schmidt et al (*Proc. Natl. Acad. Sci. USA*, 1989, 88: 365–369). Isoform II has been purified and characterized by Kawai et al (*J. Biological Chemistry*, 1991, 266: 12544–47). Isoform III has been purified and characterized by Pollock et al (*Proc. Natl. Acad. Sci. USA*, 1991, 88: 10480–4). Isoform-specific agents may offer the advantage of selectivity, i.e., desired therapeutic effect with fewer or more tolerable side-effects.

Compounds which act directly to regulate NO synthesis or in an indirect fashion to regulate the production of cGMP through regulation of the effect of endogenous EDRF (NO) on soluble guanylate cyclase are useful in the treatment of those disease states associated with smooth muscle and smooth muscle tone, especially those involving airway, gastrointestinal and vascular muscle, and platelet function. Examples of such conditions include hypotension, endotoxemia, shock, sepsis, rhinitis, hypertension, and cerebral vasoconstriction and vasodilation, such as migraine and non-migraine headache, ischemia, thrombosis, and platelet aggregation, including preservation and processing of platelets for transfusions and perfusion technologies. Additional examples include atherosclerosis, diseases of the bronchial passages, such as asthma, diseases of the optic musculature, diseases of the gastrointestinal system, such as reflux esophagitis (GERD), spasm, diarrhea, irritable bowel syndrome, and other gastrointestinal motile dysfunctions. Such compounds may also find use in angioplasty and the treatment of sickle cell anemia.

Examples of known compounds that act to regulate the production of cGMP by this method may be grouped into four categories: (1) those compounds, for example, methylene blue, which directly or indirectly (through superoxide anion) oxidize EDRF (NO) and thereby inactivate it (R. J. Gryglewski et al., *Nature*, 1986, 320: 454–6 and S. Moncada et al., *Proc. Natl. Acad. Sci. USA*, 1986, 83: 9164–68); (2) those agents, for example, hemoglobin, which directly bind either EDRF (NO) itself or one of its end products; (3) those agents which remove superoxide anion ($O_2$)$^-$ and other oxidants, thereby enhancing the effect of EDRF (for example, the enzyme superoxide dismutase removes superoxide anion by convening it to molecular oxygen ($O_2$) and hydrogen peroxide); and (4) the nitrovasodilators, such as nitroglycerin, which provide nitrogen oxide to stimulate guanylate cyclase (F. Murad, *J. Clin. Invest.*, 1986, 78: 1–5). With the exception of the nitrovasodilators, none of these categories of compounds has provided a viable therapeutic agent for the regulation of cGMP production in disease states. The nitrovasodilators, because they provide nitrogenous oxides indiscriminately to numerous target tissues, and thus lead to such complications as tolerance (A. Mulsch et al., *European J. Pharmacol.*, 1988, 158: 191–8), may not be the ultimate therapeutic agents of choice. More recently it has been reported that N-hydroxyarginine is a substrate for the NO synthase enzyme (Steuhr et al., *J. Biol. Chem.*, 1991, 266: 6259).

SUMMARY Of THE INVENTION

The present invention is directed to regulators of nitric oxide synthase that indirectly modulate cyclic guanosine monophosphate (cGMP) production which have the formula:

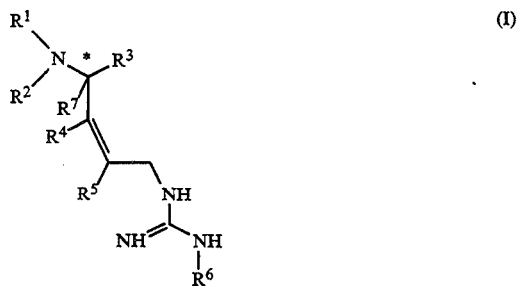

or a pharmaceutically-acceptable salt, ester, amide or prodrug thereof.

It is also directed to pharmaceutical compositions comprising a therapeutically-effective amount of a compound of formula (I) and a pharmaceutically-acceptable carrier or diluent, to intermediates useful in the preparation of compounds of formula (I); and to a method of treating disorders of vascular smooth muscles or diseases of the cartilage, macrophages, neurons, platelets, bronchial smooth muscles, optic muscles and gastrointestinal smooth muscles, in addition to treating sickle cell anemia, diabetes, synovitis, chondroarthritis and osteoarthritis, by administration of a compound of formula (I) to humans and mammals in need of such treatment.

DETAILED DESCRIPTION OF THE INVENTION

This invention relates to novel unsaturated guanidino compounds and pharmaceutical compositions thereof which regulate nitric oxide synthase and thereby indirectly modulate levels of cyclic guanosine monophosphate. These compounds may, therefore, be used in the treatment of disorders of vascular smooth musculature, macrophages, or neurons, such as hypotension, endotoxemia, sepsis, hypertension, shock, cerebral vasoconstriction, cerebral vasodilation, or headache; in disease states involving platelet aggregation, including preparation of platelets for transfusion; in angioplasty, ischemia, thrombosis, coronary vasospasm, cardiomyopathy, atherogenesis, atherosclerosis, sickle cell anemia and diabetes; in diseases involving the bronchial passages such as asthma; in diseases of the optic musculature; and in diseases of the gastrointestinal system, such as diarrhea, irritable bowel syndrome, spasm, and esophagitis (GERD).

In particular, the invention is directed to compounds of formula (I):

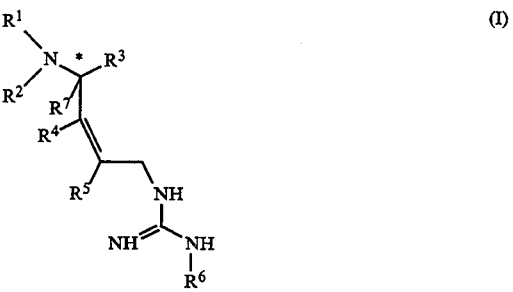

or a pharmaceutically-acceptable salt, ester, amide or prodrug thereof, wherein

\* represents a potential chiral center;

$R^1$ and $R^2$ are independently selected from the group consisting of:
(1) hydrogen;
(2) $C_1$–$C_6$-alkyl;
(3) $C_6$–$C_{12}$-aryl, as defined below;
(4) substituted $C_6$–$C_{12}$-aryl, as defined below;
(5) $C_6$–$C_{12}$-aryl-$C_1$–$C_4$-alkyl, as defined below;
(6) substituted $C_6$–$C_{12}$-aryl-$C_1$–$C_4$-alkyl, as defined below;
(7) $C_2$–$C_6$-alkenyl, as defined below;
(8) N-protecting group, as defined below;
(9) —CO-$C_1$–$C_6$-alkyl;
(10) —CO-$C_6$–$C_{12}$-aryl;
(11) —CO-substituted $C_6$–$C_{12}$-aryl;
(12) —CO-($C_6$–$C_{12}$-aryl-$C_1$–$C_4$-alkyl); and
(13) —CO-(substituted $C_6$–$C_{12}$-aryl-$C_1$–$C_4$-alkyl);

$R^3$ is selected from the group consisting of:
(1 hydrogen);
(2) $C_1$–$C_6$-alkyl;
(3) $C_2$–$C_6$-alkenyl;
(4) CH(OH)—$R^8$, wherein $R^8$ hydrogen, $C_1$–$C_6$-alkyl or $C_6$–$C_{12}$-aryl; and
(5) CH(O$R^9$)—$R^8$, wherein $R^8$ is defined as above, and $R^9$ is $C_1$–$C_6$-alkyl or a hydroxy protecting group, as defined below;

$R^4$ is hydrogen or $C_1$–$C_4$-alkyl;
$R^5$ is hydrogen, $C_1$–$C_4$-alkyl or halogen;
$R^6$ is selected from the group consisting of:
(1) hydrogen;
(2) $C_1$–$C_6$-alkyl;
(3) $C_6$–$C_{12}$-aryl-$C_1$–$C_6$-alkyl;
(4) cyano;
(5) nitro;
(6) hydroxy;
(7) amino;
(8) —O$R^{10}$, wherein $R^{10}$ is a hydroxy protecting group; and
(9) —NH$R^{11}$, wherein $R^{11}$ is an N-protecting group; and $R^7$ is hydrogen or $C_1$–$C_4$-alkyl.

In one embodiment of the present invention are compounds represented by formula (Ia):

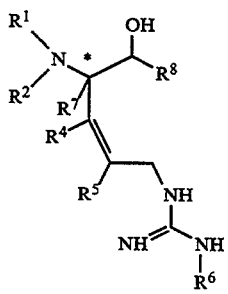

(Ia)

wherein $R^1$, $R^2$, $R^4$, $R^5$, $R^6$, $R^7$, and $R^8$ are as defined above. In a preferred embodiment, $R^1$, $R^2$, $R^4$, $R^5$, $R^7$, and $R^8$ are hydrogen and $R^6$ is nitro.

Representative of the compounds of the invention are:
$N^G$-Nitroguanidinyl-4(S)-amino-pent-2,Z-ene-5-ol;
4-Amino-1-$N^G$-nitroguanidino-5-methoxy-(4,S)-2,Z-pentene;
$N^4$-Methyl-4-amino-1-($N^G$-nitroguanidino)-(4,S)-2,Z-penten-5-ol;
1-$N^G$-(Nitroguanidino)-4-amino-2,Z-butene;
$N^G$-Nitroguanidinyl-4(R)-amino-pent-2,Z-ene-5-ol;
$N^G$-Aminoguanidino-4(S)-amino-pent-2,Z-ene-5-ol; and
$N^G$-Methylguanidinyl-4(S)-amino-pent-2,Z-ene-5-ol.

Representative of the preferred compounds of the invention are:
$N^G$-Nitroguanidinyl-4(S)-amino-pent-2,Z-ene-5-ol;
1-$N^G$-(Nitroguanidino)-4-amino-2,Z-butene;
$N^G$-Nitroguanidinyl-4(R)-amino-pent-2,Z-ene-5-ol; and
$N^G$-Aminoguanidino-4(S)-amino-pent-2,Z-ene-5-ol.

"$C_2$–$C_6$-Alkenyl" refers to a straight or branched chain radical from 2-to-6 carbon atoms, which contains at least one carbon-carbon double bond.

"Alkoxy", refers to $R^{19}$O—, wherein $R^{19}$ is either a $C_1$–$C_4$- or a $C_1$–$C_6$-alkyl group, as specified.

"Alkoxycarbonyl" refers to $A^2$O—C(O)—, wherein $A^2$ is a $C_1$–$C_4$-alkyl group, and includes, for example, methoxycarbonyl, ethoxycarbonyl, n-propyloxycarbonyl, isopropyloxycarbonyl, n-butyloxycarbonyl, isobutyloxycarbonyl and t-butyloxycarbonyl.

"Alkyl" refers to straight- or branched-chain alkyl radicals containing from 1-to-3 carbon atoms ("$C_1$–$C_3$-alkyl"), 1-to-4 carbon atoms ("$C_1$–$C_4$-alkyl") or from 1-to-6 carbon atoms ("$C_1$–$C_6$-alkyl") including, but not limited, to methyl, ethyl, n-propyl, isopropyl, n-butyl, isobutyl, sec-butyl, n-pentyl, 2-methylbutyl, 2,2-dimethylpropyl, n-hexyl, 2-methylpentyl, 2,2-dimethylbutyl, n-hexyl, and the like.

"$C_6$–$C_{12}$-Aryl" or "$C_6$–$C_{12}$-aryl group", as used herein, refers to carbocyclic aromatic isolated or fused rings of from 6-to-12 carbon atoms, for example, phenyl, naphthyl, indanyl, fluorenyl, terahydronaphthyl, indenyl, or isoindenyl.

"$C_6$–$C_{12}$-Aryl-$C_1$–$C_4$-alkyl" refers to a $C_6$–$C_{12}$-aryl group, as defined above, appended to a $C_1$–$C_4$-alkyl radical, as defined above, including, but not limited to, benzyl, phenylethyl, naphthylmethyl, and the like.

"$C_6$–$C_{12}$-Aryloxy" refers to $R^{22}$O—, wherein $R^{22}$ is an $C_6$–$C_{12}$-aryl group, as defined above.

"Cyclo-$C_3$–$C_7$-alkyl" refers to an alicyclic saturated ring having from 3-to-7 carbon atoms, including but not limited to, cyclopropyl, cyclobutyl, cyclopentyl, cyclohexyl, and the like.

"Halogen" refers to fluoro (F), chloro (Cl), bromo (Br) and iodo (I).

"Halo-$C_1$–$C_2$-alkyl" refers to a $C_1$–$C_4$-alkyl radical, as defined above, in which one to three hydrogen atoms have been replaced by a halogen, including, but not limited to, chloromethyl, 2-fluoroethyl, trifluoromethyl, and the like.

"Het", as used herein, refers to aromatic or fused aromatic rings of from 2 to 11 carbon atoms and from 1-to-3 heteroatoms independently selected from the group consisting of nitrogen, oxygen and sulfur. Representative Het compounds include, but are not limited to, pyrrolyl, pyridyl, indolyl, quinolinyl, benzimidazolyl, furyl, thienyl, benzothienyl, pyrazolyl, pyrazidinyl, isoquinolinyl, oxazolyl, isoxazolyl, thiazolyl, imidazolyl, and the like.

"Hydroxy-protecting group" or "O-protecting group" refers to a substituent which protects hydroxyl groups against undesirable reactions during synthetic procedures and includes, but is not limited to, substituted methyl ethers, for example, methoxymethyl, benzyloxymethyl, 2-methoxyethoxymethyl, 2-(trimethylsilyl)ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

"N-Protecting group", "nitrogen-protecting group" or "N-protected" refers to those groups intended to protect an amino group or the N-terminus of an amino acid or peptide against undesirable reactions during synthetic procedures or to prevent the attack of exopeptidases on the compounds or to increase the solubility of the compounds, and includes, but is not limited to, sulfonyl; acyl, such as acetyl, pivaloyl and benzoyl; alkoxycarbonyl, such as t-butyloxycarbonyl (Boc) and carbobenzyloxy (Cbz); and α-aminoacyl residues, which may themselves be similarly N-protected. Other intended groups may be found in Volume 3 of *The Peptides*, E. Gross and J. Meinhofer, editors, Academic Press, 1981.

"Pharmaceutically-acceptable ester" refers to the pharmaceutically-acceptable, nontoxic esters of the compounds of the present invention which include $C_1$–$C_6$-alkyl esters, wherein $C_1$–$C_6$-alkyl is as defined above, and $C_5$–$C_7$-cycloalkyl esters, wherein $C_5$–$C_7$-cycloalkyl refers to cyclic saturated hydrocarbon radicals, such as cyclopentyl, cyclohexyl, and the like. Also included are $C_6$–$C_{12}$-aryl-$C_1$–$C_6$-alkyl esters, wherein $C_6$–$C_{12}$-aryl-$C_1$–$C_6$-alkyl are as defined above. Representative examples include benzyl, phenethyl, and the like.

"Pharmaceutically-acceptable salts" refers to the pharmaceutically-acceptable, nontoxic, inorganic or organic acid addition salts of the compounds of the present invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitate, methanesulfonate, stearate, laurate, borate, benzoate, lactate, phosphate, tosylate citrate, maleate, fumarate, succinate, tartrate, napsylate, and the like.

"Polypeptide chain", as used herein, refers to a series of from 1-to-6 amino acids joined by amide linkages which may be branched or linear, wherein the amino acids are selected independently from naturally-occurring amino acids, including but not limited to glycine, alanine, leucine, valine, phenylalanine, proline, methionine, tryptophan, asparagine, aspartic acid, glutamic acid, glutamine, serine, threonine, lysine, arginine, tyrosine, histidine, ornithine and the like.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, vol. 14 of the A.C.S. Symposium Series, American Chemical Society (1975). Examples of esters useful as prodrugs for compounds containing carboxyl groups can be found on pages 14–21 of *Bioreversible Carriers in Drug Design: Theory and Application*, edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

The term "protecting group" is well known in the art and refers to sustituents on functional groups of compounds undergoing chemical transformation which prevent undesired reactions and degradations during a synthesis; see, for example, T. H. Greene, *Protective Groups in Organic Synthesis*, John Wiley & Sons, (1981).

"Substituted $C_3$–$C_4$-alkenylene" refers to alkenylene groups wherein, in each case, one of the carbon atoms in the alkenylene chain is substituted with one-or-two substituents independently selected at each occurrence from the group consisting of (i) halogen, (ii) $C_1$–$C_4$-alkyl, (iii) $C_1$–$C_2$-haloalkyl, (iv) $C_6$–$C_{12}$-aryl-$C_1$–$C_6$-alkyl, and (v) substituted $C_6$–$C_{12}$-aryl-$C_1$–$C_6$-alkyl.

"Substituted $C_6$–$C_{12}$-aryl" refers to a $C_6$–$C_{12}$-aryl group, as defined above, substituted with one, two, or three substituents independently selected from $C_1$–$C_4$-alkyl, $C_1$–$C_4$-alkoxy, $C_1$–$C_4$-thioalkoxy, carboxy, carbo-$C_1$–$C_4$-alkoxy, nitro, halo-$C_1$–$C_4$-alkyl, hydroxy, amino, and $C_1$–$C_4$-alkylamino.

"Substituted $C_6$–$C_{12}$-aryl-$C_1$–$C_4$-alkyl" refers to a $C_6$–$C_{12}$-aryl group, as defined above, appended to a $C_1$–$C_4$-alkyl radical, as defined above.

"Substituted $C_6$–$C_{12}$-aryloxy" refers to a $A^3O$— group, wherein $A^3$ is a substituted $C_6$–$C_{12}$-aryl group, as defined above.

By a "therapeutically-effective amount" of the compound of the invention is meant a sufficient amount of the compound to treat disorders, at a reasonable benefit/risk ratio applicable to any medical treatment. It will be understood, however, that the total daily usage of the compounds and compositions of the present invention is to be decided by the attending physician within the scope of sound medical judgment. The specific therapeutically-effective dose level for any particular patient will depend upon a variety of factors including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts and well within the capabilities of attending physicians.

The following abbreviations are used herein: BOC or Boc for t-butyloxycarbonyl, Bz for benzyl, CBZ for benzyloxycarbonyl, CDCl₃ for deuterochloroform, D₂O for deuterium oxide, DCC for dicyclohexylcarbodiimide, DIBAL for diisobutylaluminum hydride, DIEA for diisopropylethylamine, DMAP for dimethylaminopyridine, DMF for N,N-dimethylformamide, DMSO for dimethylsulfoxide, DMSO-d₆ for deuterodimethylsulfoxide, EDCl for 1-(3-dimethylaminopropyl)-3-ethylcarbodiimide hydrochloride, EtOH for ethanol, HOAc for acetic acid, IBCF for isobutyl chloroformate, LAH for lithium aluminum hydride, Ms for methanesulfonyl, NH₄OAc for ammonium acetate, NMM for N-methylmorpholine and TEA for triethylamine, PAW for pyridine/acetic acid/water (20:6:11), TFA for trifluoroacetate, THF for tetrahydrofuran, and TMSi for trimethylsilyl.

Amino acids are herein designated as the natural L-isomer or as the D-isomer in accordance with convention, or chiral compounds, including amino acids, are assigned the R, S, or (R,S) configuration at the chiral center. Preferred compounds of the present invention are those which have the S configuration at the alpha-carbon atom, i.e., the carbon atom in the formula (I) designated by an *. The terms "R" and "S" configuration used herein are as defined by IUPAC (*IUPAC 1974 Recommendations for Section E. Fundamental Stereochemistry, Pure Appl. Chem.*, 1976, 45: 13–30.)

The compounds of the present invention may be used in the form of pharmaceutically-acceptable salts derived from inorganic or organic acids. These salts include, but are not limited to, the following: acetate, adipate, alginate, aspartate, benzoate, benzenesulfonate, bisulfate, butyrate, camphorate, camphorsulfonate, citrate, cyclopentanepropionate, digluconate, dodecylsulfate, ethanesulfonate, flavianate, fumarate, glucoheptonate, glycerophosphate, hemisulfate, heptanoate, hexanoate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, phosphate, picrate, pivalate, propionate, succinate, tartrate, thiocyanate, tosylate, and undecanoate.

Appropriate cationic salts are also readily prepared by conventional procedures such as treating an acid of formula I with an appropriate amount of base, such as an alkali or alkaline earth metal hydroxide e.g. sodium, potassium, lithium, calcium, or magnesium, or an organic base such as an amine, e.g., dibenzylethylenediamine, cyclohexylamine, dicyclohexylamine, triethylamine, piperidine, pyrrolidine, benzylamine, and the like, or a quaternary ammonium hydroxide such as tetramethylammonium hydroxide and the like. Also, the basic nitrogen-containing groups can be quaternized with such agents as loweralkyl halides, including methyl, ethyl, propyl, and butyl chlorides, bromides, and iodides; dialkyl sulfates; long chain halides such as decyl, lauryl, myristyl, and stearyl chlorides, bromides and iodides; arylalkyl halides like benzyl and phenethyl bromides, and others. Water or oil-soluble or dispersible products are thereby obtained.

The salts of the present invention may be synthesized from the compounds of formula I which contain a basic or acidic moiety by conventional methods, such as by reacting the free base or acid with stoichiometric amounts or with an excess of the desired salt forming inorganic or organic acid or base in a suitable solvent or various combinations of solvents.

When a compound of formula (I) is used in a human subject, the total daily dose administered in single or divided doses may be in amounts, for example, from about 0.01 to about 50 mg/kg body weight, or more usually, from about 0.2 to about 30 mg/kg body weight. Single dose compositions may contain such amounts or submultiples thereof to make up the daily dose. In general, treatment regimens according to the present invention comprise administering to a patient in need of such treatment from about 20 mg to about 2000 mg of the compound(s) of this invention per day in multiple doses or in a single dose.

The amount of active ingredient that may be combined with the carrier materials to produce a single dosage form will vary depending upon the host treated, the particular treatment and the particular mode of administration.

The compounds of the present invention may be administered orally, parenterally, by inhalation spray, rectally, or topically in dosage unit formulations containing conventional nontoxic pharmaceutically-acceptable carriers, adjuvants, and vehicles as desired. The term parenteral as used herein includes subcutaneous injections, intravenous, intramuscular, intrasternal injection, or infusion techniques.

Liquid dosage forms for oral administration may include pharmaceutically-acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butandiol. Among the acceptable vehicles and solvents that may be employed are water, Ringer's solution, isotonic sodium chloride solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

The injectable formulation can be sterilized, as for example by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Dosage forms for topical or transdermal administration of a compound of this invention include ointments, pastes, creams, lotions, gels, powders, solutions, sprays, inhalants or patches. The active component is admixed under sterile conditions with a pharmaceutically-acceptable carrier and any needed preservatives or buffers as may be required. Ophthalmic formulations, ear drops, eye ointments, powders and solutions are also contemplated as being within the scope of this invention.

The present agents can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to the compounds of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Vol. XIV, Academic Press, New York, N.Y. 1976, pp. 33 et seq.

The compounds of this invention may be administered alone or in combination or in concurrent therapy with other agents.

The foregoing is merely illustrative of the invention and is not intended to limit the invention to the disclosed compounds. Variations and changes which are obvious to one skilled in the art are intended to be within the scope and nature of the invention which are defined in the appended claims.

SYNTHESIS OF THE COMPOUNDS OF THE INVENTION

In general compounds of the current invention may be prepared in the following ways: starting with a D, L, or D,L $\beta$-hydroxy-$\alpha$-amino acid (1) (the R enantiomer at the $\alpha$ carbon center is shown for illustration) N-protected with a protecting group (P) of which Boc, Cbz, Fmoc etc. are preferred, an ester (2), where R=methyl (Scheme 1 ), can be prepared via diazomethane reaction. Alternatively, compound (2) may be prepared by reacting the unprotected form of (1) with an appropriate alcohol ROH (e.g. methanol under acidic conditions). The resulting amino acid ester hydrochloride is N-protected under standard conditions to provide (2) directly. Compound (2) is reacted under mild acid conditions (e.g., p-toluenesulfonic acid) with an appropriate aldehyde, ketone, or acetal/ketal equivalent thereof ((A(CO)B) e.g., dimethoxypropane, benzaldehyde, cyclohexanone, etc.) to provide ester (3). Ester (3) is converted to the aldehyde (4) either by direct reduction with DIBAL or via the fully reduced alcohol form (e.g., further reaction with DIBAL, LAH, etc.) followed by oxidation (Swern conditions, pyridine sulfur trioxide complex, etc.). The aldehyde (4) can serve as a precursor to the secondary alcohol (5) via reaction with an appropriate nucleophile (e.g., alkylmagnesium halides, alkenylmagnesium halides, alkynyllithium reagents, alkyllithium reagents, etc.). The alcohol (5) may be oxidized to the ketone (6) (e.g., Swern oxidation, pyridine sulfur trioxide complex, pyridinium chlorochromate, etc.). Either the aldehyde (4) or the ketone (6) can then be converted to enoate (7) via the appropriate Wittig, Horner Emmons reagent or their synthetic equivalents (e.g. alkyl (triphenylphosphoranylidene-)acetate, etc.). In the case where (7) arises from compound (4), $R^4$=H. The enoate (7) can be reduced to the allylic alcohol (8) or to the intermediate reduction product aldehyde (9) Aldehyde (9) can also be obtained more directly via the oxidation of alcohol (8) under a number of conditions. The aldehyde (9) can also be converted to the alcohol (8) directly. The alcohol (8) is reacted with mesyl chloride under basic conditions (triethylamine, etc.) to provide the mesylate (10). The mesylate (10)is reacted with sodium azide to provide the azide (11). Azide (11) can be reduced under a number of conditions (e.g., sodium borohydride, palladium catalyzed hydrogenation, triphenylphosphine followed by acid hydrolysis, etc.) to provide the amine (12). Alternatively the mesylate (10) can be displaced with phthalimide to provide (13) which upon treatment with hydrazine provides amine (12). The amine (12) is guanylated with a variety of guanylation reagents (e.g., S-methyl N-nitrothiopseudothiourea, etc.) to provide the desired compound (14). Alternatively the amine nitrogen can be protected with the N-protecting group (P') to provide the intermediate (15) which can be deprotected and guanylated to provide (14).

Compound (15) is reacted with acid under hydrolytic conditions to remove the aldehydic/ketonic group (A(-CO)B) (Scheme 1, continued) and provide the compound (16). In some cases the N-protecting group (P) is labile and a second step of N-protection with (P) is required to provide (16). The alcohol (16) can be oxidized to the compound (17) provided either $R^a$ or $R^8$ is hydrogen. Compound (17) can be reacted with organometallics to provide compound (16) wherein $R^a$ and $R^8$ both do not equal hydrogen. The protecting group (P') of compound (16) is removed in a standard fashion to provide compound (18). The amine (18) can be guanylated using various guanylation reagents to then provide the compound (19). The protecting group (P) of compound (19) is removed to provide the desired compound (20). In addition, compounds of the type (14) can be reacted under acidic hydrolytic conditions when (P) is an acid labile N-protecting group to provide the desired aminoalcohol (20), directly.

An alternative sequence which also provides the desired guanidino compounds is illustrated in Scheme 2. Compounds such as (12) can be reacted with cyanogen bromide under mild basic conditions (triethylamine, etc.) to provide the cyanamide (21). An alternative sequence is the formation of the parent urea via reaction of (12) with trimethylsilylisocyanate or its equivalents (e.g. trichloroacetylisocyanate followed by basic removal of the trichloroacetyl group, etc.) and dehydration (e.g., tosylchloride in pyridine, etc.) of the parent urea to the cyanamide (21). The cyanamide (21) is reacted with nucleophiles such as $H_2NR^6$ to provide the guanidino compound (22). This sequence is particularly useful in the cases where ($H_2NR_6$ is hydrazine, substituted hydrazine, hydroxylamine, alkoxyamine, etc.). Note that likewise compound (22) can be transformed to compound (23). In a manner similar to the transformation of (12) to compound (21), compounds such as (18) can be reacted with cyanogen bromide (alternatively via the sequence involving the intermediate urea form) to produce the cyanamide (24). Compound (24) is converted to the guanidino compound (23) via removal of the protecting group P'.

Another approach to guanidino compounds is represented in Scheme 3. Compound (12) is reacted with diarylcyanocarbonimidate to provide compound (26) where in the Ph symbol represents the aryl group. Compound (26) can be reacted with a ammonia or its equivalent to provide compound (27) where in $R^8$ represents cyano group. Likewise compound (18) can be reacted with diarylcyanocarbonimidate to yield (28), and compound (28) can be reacted with ammonia to produce compound (29). Compounds (29) or (27) can be convened to desired compound (30) by simple deprotection steps.

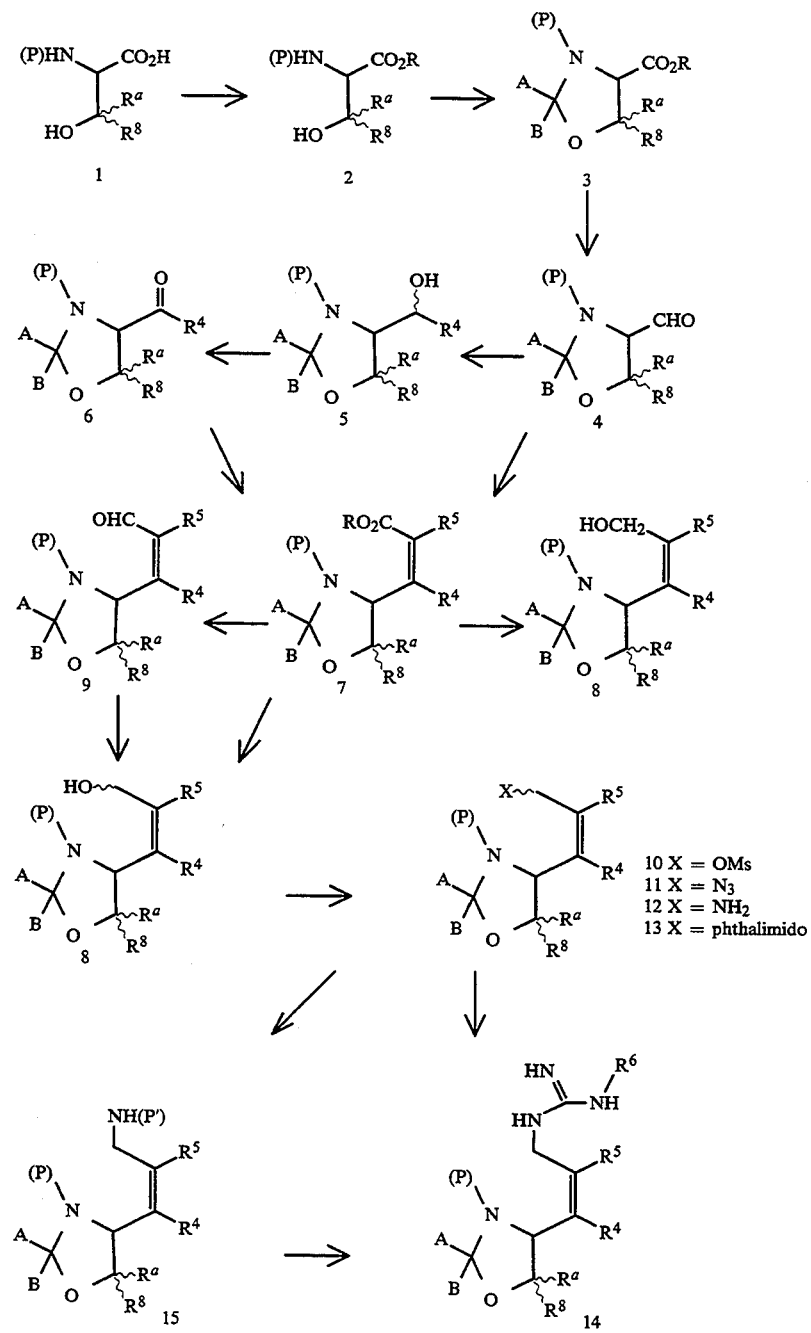

Scheme 1

-continued
Scheme 1
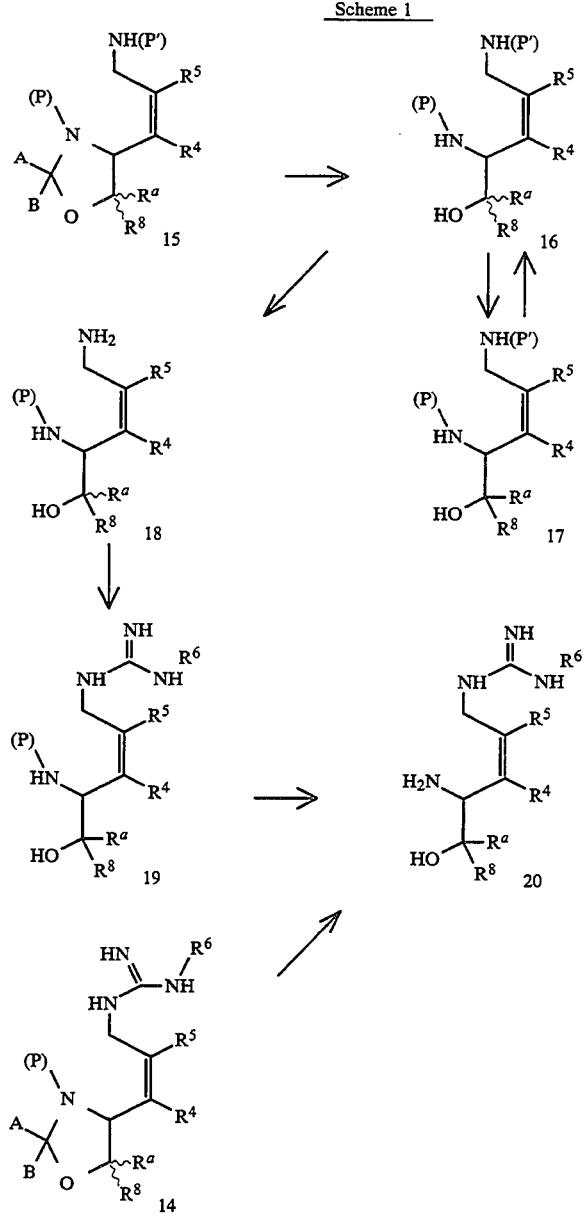
Scheme 2
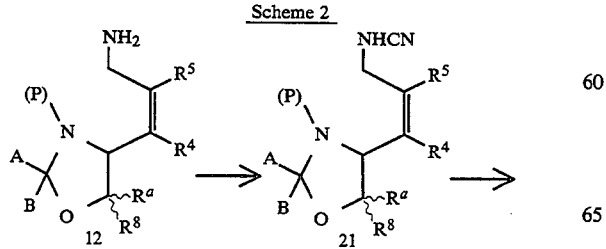
-continued
Scheme 2
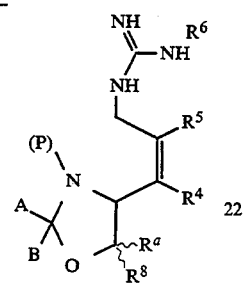

-continued
Scheme 2

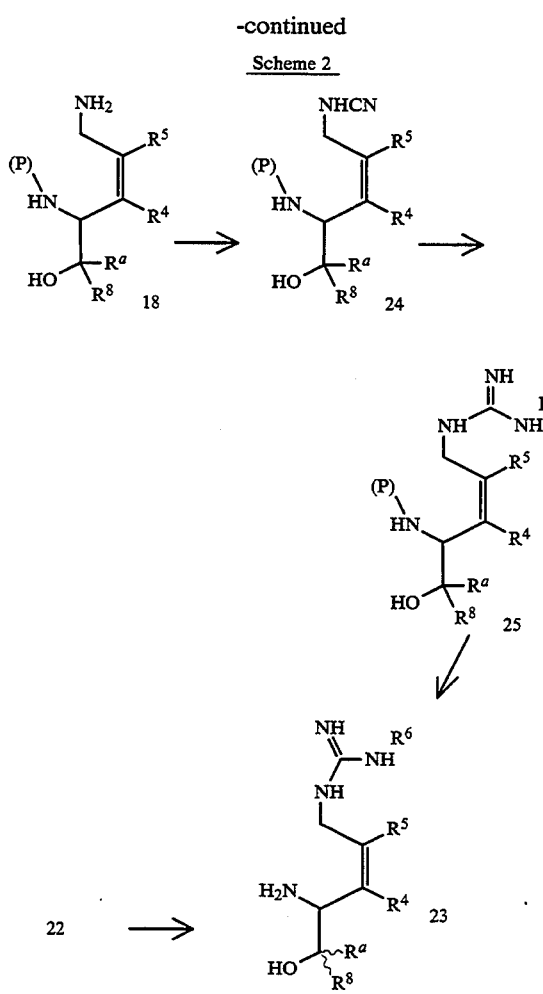

-continued
Scheme 3

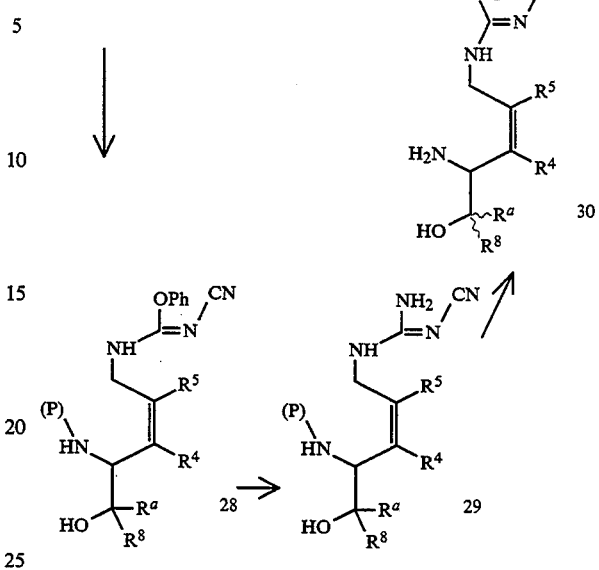

Scheme 3

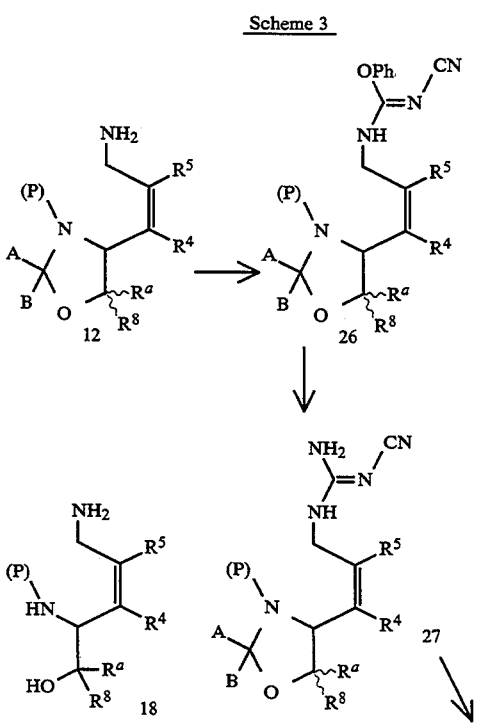

GENERAL EXPERIMENTAL PROCEDURES FOR BIOASSAYS

The enzyme NO synthase produces EDRF/NO and citrulline from L-arginine (Bredt and Snyder, Proc. Nat'l. Acad. Sci. USA, 1989, 87: 682-5). The enzymatic generation of EDRF/NO is monitored by measuring the conversion of [$^3$H]-L-arginine to [$^3$H]-L-citrulline. An inhibitor of this specific enzymatic reaction lowers the conversion rate and, thus, the amount of [$^3$H]-L-citrulline produced. Likewise, a compound acting as a substrate would compete with L-arginine and thereby lower the conversion rate.

In those instances where it is suspected that the test substance is acting as a substrate rather than an inhibitor, the EDRF/NO may be estimated. For this confirmation bioassay, a method for quantification of endothelium-derived relaxing factor (EDRF) is utilized and is described in detail below. This technique, measuring cyclic GMP responses of RFL-6 rat fetal lung fibroblast cells to estimate NO or EDRF is sensitive, simple and quite useful for the evaluation of compounds that regulate EDRF/NO release from various endothelial cells, or other cells or tissues (such as for example RAW cells (induced with LPS) and N1E-115 cells). (cf. Ishii, K., et al., American Journal of Physiology, 1991, 261: (2 pt 2) H598-603). The cyclic GMP measured is an indirect measure of the amount of EDRF/NO produced by NO synthase, so compounds that reduce the amount of cyclic GMP produced are termed inhibitors of NO synthase, and those that increase cyclic GMP in the absence of exogenous L-arginine are termed substrates or stimulators of NO synthase.

BIOLOGICAL ACTIVITY OF EXEMPLIFIED COMPOUNDS

[$^3$H]-Arginine to [$^3$H]-Citrulline Conversion

The conversion of L-arginine to L-citrulline was assayed as reported previously (Bredt and Snyder, Proc. Nat'l Acad Sci USA, 1989, 87: 682-5) with minor modifications. Briefly, samples of partially purified NO synthase, 50–100 μg of protein or 20 μL of cytosol (alternatively cytosolic preparations from RAW 264.7 cells, a murine monocyte-macrophage cell line, induced for 16 hours with 10 μg/mL medium of Lipopolysaccharide (LPS), or partially purified (phosphocellulose column) type I isozyme from rat brain cerebellum, or partially purified isozyme III from bovine aortic endothelial cells (BAE cells)) were incubated for 20 minutes (3 minutes in the cases of purified enzyme preparations) at 25° C. in the presence of 10 μM L-[2,3-$^3$H]arginine (55 C$_i$/mmol) (containing 34 nM (0.2 μC$_i$)), 1 mM NADPH, and 2 mM CaCl$_2$ in a final volume of 100 μL. The reaction was stopped by adding 1 mL of stop buffer (2 mM EGTA, 2 mM EDTA, 20 mM Hepes, pH 5.5). The total volume was then applied to a 1 mL Dowex AG 50WX-8 column (Na+ form, Bio-Rad) that had been pre-equilibrated with the stop buffer. L-[2,3-$^3$H]Citrulline was eluted (2×) with 0.5 mL of stop buffer and radioactivity was determined by liquid scintillation counting.

cGMP Assay—(Rat Fetal Lung Fibroblast (RFL-6) cells as detectors of EDRF/NO)

This is a new bioassay method for detection and quantification of endothelium-derived relaxing factor (EDRF) wherein cyclic GMP responses of RFL-6 rat fetal lung fibroblast cells are utilized to estimate the activity of nitric oxide (NO) and EDRF. The conditioned medium from bovine aortic endothelial (BAE) cells cultured in tissue culture plates (alternatively cytosolic preparations from a murine macrophage cell line—RAW cells—induced for 16 hr with 10 μg/mL medium of LPS, partially purified (phosphocellulose column) type I isozyme from rat brain cerebellum, partially purified isozyme III from BAE cells, or RAW cells cultured in tissue plates and induced for 16 hr with 10 μg/mL LPS, or N1E-115 neuroblastoma cells cultured in tissue plates) was quickly transferred to RFL-6 incubations in order to determine EDRF/NO. In the presence of superoxide dismutase, RFL-6 cells cultured in 6-well tissue culture plates exhibited very high sensitivities to both NO and EDRF: e.g., they responded to NO at a concentration as low as 2 nM and the basal release of EDRF from 1-2×10$^6$ BAE cells. Based on the lower detection limit of the radioimmunoassay for cyclic GMP, calculations reveal that 100-200 fmoles of NO and the basal EDRF release from 1-2×10$^5$ BAE cells can be detected with RFL-6 cells by choosing smaller culture wells. Thus, this method is more sensitive than any other currently available. This bioassay technique for EDRF/NO is sensitive, simple and quite useful for the evaluation of experimental conditions and compounds that regulate EDRF/NO release from various endothelial cells and other cells and tissues, for instance RAW cells (induced with LPS), N1E-115 cells, their homogenates in various states of purity and any other EDRF/NO generating system.

RFL-6 Cell Culture Method

Rat fetal lung fibroblast cells (RFL-6, Stanford University, Calif.) were grown in 6-, 12-, 24- or 48-well tissue culture plates containing F-12 Ham's nutrient mixture supplemented with 15% uninactivated fetal bovine serum. Bovine aortic endothelial (BAE) cells (NIGMS, Human Genetic Mutant Cell Repository, Camden, N.J.) were cultured in the 6-well plates containing Eagle's Minimum Essential Medium (MEM) supplemented with 20% fetal bovine serum and MEM nonessential amino acids (0.1 mM each). Both culture media contained 2 mM L-glutamate, 100 U/mL penicillin and 0.1 mg/mL streptomycin. Cells were maintained at 37° C. under an atmosphere of 95% air:5% $CO_2$.

Detection of EDRF/NO with RFL-6 Cells

BAE cells (RAW cells [induced with LPS], N1E-115 cells, rat brain homogenate passed through a phosphocellulose column, etc.) grown to confluence in 6-well plates were used as the source of EDRF/NO. After removing the culture medium, cells were washed twice with 2 mL of Lockes solution (without IBMX) and equilibrated for 20 minutes in 1 mL of Lockes buffer containing 20 U/mL of SOD in the presence or absence of 100 μM L-arginine, N$^G$-nitro-L-arginine (NNA), or the test compounds for 15 min before stimulation with 3 μM ADP for 3 minutes (no stimulation is necessary for homogenate sources of enzyme or those cells induced with LPS, neurotensin is used to stimulate N1E-115 cells). Following exposure of BAE cells to ADP for 3 minutes, an aliquot of the conditioned medium was transferred to the RFL-6 incubations with a Pipetman ® micropipette. Volumes of the conditioned medium transferred were 1000 μL, 400 μL, 200 μL and 100 μL when RFL-6 cells were incubated in the 6-, 12-, 24- and 48-well plates, respectively.

Before transferring the conditioned medium from BAE cells, RFL-6 cells cultured to confluence were washed twice with a Ca and Mg free PBS then equilibrated in Locke's buffer (with 0.3 mM IBMX, 20 U/mL of SOD). The volume for preincubation was 500 μL-1000 μL. After incubating RFL-6 cells with conditioned medium from BAE cells (or other EDRF/NO producing systems) for the indicated time periods (~3 minutes), the medium was removed and ice-cold 50 mM sodium acetate buffer (pH 4.0) was added to each well to stop the reaction followed by liquid nitrogen. Cyclic GMP levels in RFL-6 cells were determined by RIA (radioimmunoassay) or samples could be stored at −70° C. until radioimmunoassay.

For assaying pure enzyme or homogenates containing active enzyme, the following alterations are made in the procedure: after preparation of the RFL cells by preincubation, a fresh Lockes buffer is added containing SOD and IBMX as before. In addition L-arginine (100 μM), NADPH (100 μM), BH$_4$ (3 μM), calmodulin (100 u/mL when necessary) and the test compound(s) are added followed by the enzyme homogenate to a final adjusted volume of 1-2 mL. Incubations proceed at 37° C. for 3 minutes followed by the same termination steps as above. cGMP is again measured by RIA.

Table 1 summarizes data on the inhibition of [$^3$H]-citrulline formation from [$^3$H]-L-arginine by the compounds of the invention in various preparations representative of the isoforms of NOS, Types I, and II NOS as represented by rat brain cytosol and RAW 247.7 macrophage cell cytosol, respectively.

TABLE 1

| Inhibition of [$^3$H]-Citrulline Formation IC$_{50}$ (μM) | | |
|---|---|---|
| Example Number | NOS Type I rat brain cytosol | NOS Type II RAW cytosol |
| 1 | 3 | 75 |
| 2 | 10 | 35 |
| 3 | 50 | 100 |
| 4 | 2 | 12 |
| 5 | 5 | 60 |
| 6 | 9 | 45 |
| 7 | 40 | >100 |

The following examples further illustrate preparation of the novel compounds of the invention. The following abbreviations are used: THF for tetrahydrofuran, DMF for N,N-dimethylformamide, $D_2O$ for deuterium oxide, $CD_3OD$ for deuterated methanol, $CDCl_3$ for deuterochloroform, $CH_3CN$ for acetonitrile, DMSO-$d_6$ for deuterodimethylsulfoxide, Boc for t-butyloxycarbonyl, Cbz for benzyloxycarbonyl, $CH_2Cl_2$ for methylene chloride, PAW for pyridine/acetic acid/water (20:6:11), DCC for dicyclohexylcarbodiimide, DIBAL for diisobutylaluminum hydride, DIEA for diisopropylethylamine, EDCI for 1-(3-dimethyl-aminopropyl)-3-ethylcarbodiimide hydrochloride, EtOH for ethanol, $Et_2O$ for diethyl ether, EtOAc for ethyl acetate, IBCF for isobutyl chloroformate, hr for hours, HOAc for acetic acid, HCl for hydrochloric acid, HOBT for 1-hydroxybenzotriazole, $H_2O$ for water, LAH for lithium aluminum hydride, MeOH for methanol, $MgSO_4$ for magnesium sulfate, $NH_4OAc$ for ammonium acetate, NaOH for sodium hydroxide, $Na_2SO_4$ for sodium sulfate, $NaHCO_3$ for saturated sodium bicarbonate, $NH_4OH$ for ammonium hydroxide, NMM for N-methylmorpholine, rt for room temperature, TFA for trifluoroacetic acid and TEA for triethylamine.

EXAMPLE 1

$N^G$-Nitroguanidinyl-4(S)-amino-pent-2,Z-ene-5-ol

Step 1a. N-[(1,1-Dimethylethoxy)carbonyl]-D-serine methyl ester

To a solution of D-Boc-serine (25 mmol) in ethanol cooled to 0° C. was added diazomethane (4–5 eq) in a solution of $Et_2O$. After the addition of the diazomethane, the reaction was stirred for one hour and then quenched with glacial HOAc. The product was extracted with EtOAc. The combined organic extracts were washed with $NaHCO_3$ and brine, dried over $MgSO_4$, and concentrated in vacuo. Purification by flash chromatography eluting with hexane/EtOAc (1:1) afforded the product (72%) as a yellow liquid: $R_F$ 0.75 (EtOAc:hexane 1:1); $^1$H NMR (300 MHz, $CDCl_3$) δ: 1.47 (s, 9H), 2.48 (s, 1H), 3.82 (s, 3H), 3.90 (dd, J=4, 12 Hz, 1H), 3.95 (dd, J=4, 12 Hz, 1H), 4.40 (m, H), 5.45 (m, H); $^{13}$C NMR (75 MHz, $CDCl_3$) δ: 21.16, 52.47, 55.63, 60.38, 63.14, 80.17, 155.71, 171.39; MS(DCI/$NH_3$) m/e 220 (m+H)$^+$, 237 (m+$NH_4$)$^+$. Analysis calc'd for $C_9H_{17}NO_5 \cdot 0.5\ H_2O$: C, 47.36; H, 7.95; N, 6.14. Found: C, 47.20; H, 7.58; N, 6.12.

Step 1b. 3-(1,1-Dimethylethyl) 4-methyl-(R)-2,2-dimethyl-3,4-oxazolidinecarboxylate To a solution of the methyl ester of Example 1a (4.8 mmol) in benzene was added 2-methoxypropane (2 eq) and p-toluene sulfonic acid (0.1 eq), and the reaction was heated to reflux for 48 hr. The reaction was extracted with EtOAc and the combined organic extracts were washed with brine and water, dried over $MgSO_4$ and concentrated in vacuo. Purification by flash chromatography eluting with EtOAc and hexane afforded the product as a yellow liquid in 78% yield: $R_F$ 0.5 (1:1 hexane:EtOAc); $^1$H NMR (300 MHz, $CDCl_3$) δ: 1.50 (s, 9H), 1.55 (br s, 3H), 1.64 (s, 3H), 3.80 (s, 3H), 4.25 (m, 1H), 4.38 (dd, J=6, 9 Hz, 1H), 4.50 (dd, J=6, 8.5 Hz, 1H); MS(DCI/$NH_3$) m/e 260 (m+H)$^+$, 277 (m+$NH_4$)$^+$, 221 (m-$C_4H_9$). Analysis calc'd for $C_{12}H_{21}NO_5 \cdot 0.75\ CH_2Cl_2$: C, 47.41; H, 7.02; N, 4.34. Found: C, 46.86; H, 6.67; N, 4.29.

Step 1c. 1,1-Dimethylethyl (R)-4-formyl-2,2-dimethyl-3-oxazolidinecarboxylate

To a solution of the methyl ester of Example 1b (17.8 mmol) in toluene cooled to −78° C. was added 1M DIBAL (2.2 eq) over a 15–20 minute period. The reaction was stirred for 3–4 hr at −78° C. and then quenched with $CH_3OH$ at −78° C. The reaction was extracted with EtOAc and the combined organic extracts were washed with sodium hydroxide, water and brine, dried over $MgSO_4$ and concentrated in vacuo to afford the product as a colorless oil (64%): $R_F$ 0.45 (1:1 EtOAc:hexane); $^1$H NMR (300 MHz, $CDCl_3$) δ: 1.49 (s, 9H), 1.52 (s, 3H), 1.58 (s, 3H), 3.80 (m, 1H), 4.20 (m, 2H), 4.40 (m, 1H), 9.53 (br s, 1H); MS(DCI/$NH_3$) m/e 230 (m+H)$^+$, 247 (m+$NH_4$)$^+$, 191 (m-$C_4H_9$); $[\alpha]_D^{20°} = -24.72°$ (C=1.0, EtOH).

Step 1d. 3-(1,1-Dimethylethyl)-(S)-4-(3-(methoxypropen-2,Z-oyl))-2,2-dimethyl-3-oxazolidinecarboxylate To a −78° C. solution of anhydrous THF under a $N_2$ atmosphere was added 18-crown-6 (2.0 eq) and the bis(2,2,2-trifluoroethyl)(methoxycarbonylmethyl)phosphonate (1.0 eq) and the solution was stirred for 15 min. After 15 min the potassium bis(trimethylsilyl)amide (1.0 eq, as an 0.5M solution in toluene) was added and stirred for 10 min. A solution of aldehyde from Example 1c (1.0 eq) was added in 60 mL of THF over a 10 minute period and the reaction was stirred for 45 min. The reaction mixture was poured into $H_2O$ and shaken. $CH_2Cl_2$ (300 mL) was added and shaken. The $CH_2Cl_2$ layer was dried over $Na_2SO_4$ and concentrated in vacuo. The material was purified on neutral silica and eluted with EtOAc/hexane 1/1. This provided a 74% yield of the desired material (white solid): $R_F$ 0.50 (EtOAc/hexane 1/1); $[\alpha]_D^{20°} = +33.21°$ (c=1.15, $CH_2Cl_2$). $^1$H NMR (300 MHz, $CDCl_3$) δ: 1.40 (s, 3H), 1.48 (s, 9H), 1.53 (s, 3H), 1.62 (s, 3H), 3.80 (dd, J=5, 9 Hz, 1H), 4.27 (m, 1H), 5.38 (t, J=7.5 Hz, 1H), 5.85 (d, J=6 Hz, 1H), 6.27 (m, 1H); MS(DCI/$NH_3$) m/e 286 (M+H$^+$), 303 (M+$NH_4^+$); Analysis calc'd for $C_{14}H_{23}NO_5$: C, 58.93, H, 8.12, N, 4.91; found C, 58.84, H, 8.08, N, 4.79.

Step 1e. 3-(1,1-Dimethylethyl)-(S)-4-(3-hydroxypropen-1,Z-yl)-2,2-dimethyl-3-oxazolidinecarboxylate To a −78° C. solution of anhydrous toluene (φCH$_3$) under a $N_2$ atmosphere was added the methyl ester from Example 1d (1.0 eq) and the compound was stirred in φCH$_3$ until the reaction temperature was −78° C. DIBAL (4.5 eq) was added to the reaction via $N_2$ pressure and was added at a rate to maintain the internal reaction temperature below −68° C. The reaction was stirred at −78° C. for 1.5 hr, then the reaction was quenched with $CH_3OH$ at −78° C., and the reaction mixture was poured into 1M Rochelle salt solution and stirred for 40 min. The reaction was allowed to settle and the organic layer was decanted off. The organic layer was diluted by 30% with EtOAc, washed with brine, and dried over $Na_2SO_4$. The reaction was concentrated in vacuo. The product was purified over neutral silica gel and eluted with EtOAc/hexane 1/1. The reaction resulted in a 79% yield of the desired material (colorless oil): $R_F$ 0.30 (EtOAc/hexane 1/1 ); $[\alpha]_D^{20°} = -33.61°$ (c=0.83, $CH_2Cl_2$) $^1$H NMR (300 MHz, $CDCl_3$) δ: 1.47 (s, 9H), 1.49 (s, 3H), 1.56 (s, 3H), 3.70 (dd, J=5, 11 Hz, 1H), 4.05 (m, 2H), 4.45 (dt, J=6, 9 Hz, 1H), 4.95 (m, 1H), 5.54 (t, J=12 Hz, 1H), 5.87 (m, 1H); MS(DCI/NH3) m/e 258 (M+H$^+$), 275 (M+$NH_4^+$); Analysis calc'd for $C_{13}H_{23}NO_4$: C, 60.68, H, 9.01, N, 5.44; found C, 60.30, H, 8.96, N, 5.31.

Step 1f. 3-(1,1-Dimethylethyl)-(S)-4-(3-mesyloxypropen-1,Z-yl)-2,2-dimethyl-3-oxazolidinecarboxylate To a solution of the alcohol from Example 1e in $CH_2Cl_2$ (1.0M) at 0° C. under a $N_2$ atmosphere was added TEA (1.5 eq) and methanesulfonyl chloride (1.1 eq) and the reaction was allowed to warm to rt and stirred for 1 hour. The reaction was poured into $CH_2Cl_2$ and washed with cold water, 1N HCl, NaHCO$_3$ and brine. The organic layer was dried over $Na_2SO_4$ and concentrated in vacuo. The reaction produced a quantitative yield of the desired material, yellow oil): $R_F$ 0.70, (EtOAc/hexane 1/1); $^1$H NMR (300 MHz, CDCl$_3$) δ: 1.47 (s, 9H), 1.51 (s, 3H), 1.57 (s, 3H), 1.65 (s, 3H), 3.72 (dd, J=6, 12 Hz, 1H), 4.08 (m, 1H), 4.92 (m, 2H), 5.73 (m, 2H); MS(DCI/NH3) m/e 336 (M+H+).

Step 1g. 3-(1,1-Dimethylethyl)-(S)-4-(3-phthalamido-propen-1,Z-yl)-2,2-dimethyl-3-oxazolidinecarboxylate To a solution of the mesylate from Example 1f in anhydrous DMF (1.0M) under a $N_2$ atmosphere at rt was added potassium phthalimide and the reaction was heated at 80° C. for 16 hr. The reaction was poured into EtOAc and washed with $H_2O$, brine and added over $Na_2SO_4$. The organic layer was concentrated in vacuo. The material was purified on neutral silica, eluting with EtOAc/hexane 1/1. The material was a white solid and was obtained in 83%: $R_F$ 0.80, (EtOAc/hexane 1/1); $^1$H NMR (300 MHz, CDCl$_3$) δ: 1.48 (s, 9H), 1.55 (s, 3H), 1.61 (s, 3H), 3.62 (dd, J=5, 9 Hz, 1H), 4.22 (t, J=7 Hz, 2H), 4.60 (m, 1H), 5.00 (m, 1H), 5.63 (m, 1H), 7.71 (dd, J=4, 6 Hz, 2H), 7.85 (dd, J=4, 6 Hz, 2H); MS(DCI/NH3) m/e 387 (M+H+), 404 (M+NH4+); Analysis calc'd for $C_{21}H_{26}N_2O_5$: C, 64.27, H, 6.78, N, 7.25; found C, 64.48, H, 6.64, N, 7.00.

Step 1h. 3-(1,1-Dimethylethyl)-(S)-4-(3-aminopropen-1,Z-yl)-2,2-dimethyl-3-oxazolidinecarboxylate To a solution of the phthalimide from Example 1 g (1.0 eq) in $CH_3OH$ under a $N_2$ atmosphere was added hydrazine (4.0 eq) and the reaction was stirred and heated to 40° C. for 24 h. The reaction was cooled to rt and poured into EtOAc, washed with $H_2O$, brine and dried over $Na_2SO_4$. The material was purified on neutral silica gel, eluting with $CH_2Cl_2/CH_3OH/NH_4OH$ 80/20/1. The product was a slightly yellow oil and was obtained in 79% yield: $R_F$ 0.30 ($CH_2Cl_2$/EtOH/N-$H_4OH$ 80/20/1); $[\alpha]_D^{20°}=-57.00°$ (c=0.80, $CH_2Cl_2$) $^1$H NMR (300 MHz, CDCl$_3$) δ: 1.48 (s, 9H), 1.50 (s, 3H), 1.58 (s, 3H), 3.28 (m, 1H), 3.67 (dd, J=5, 9 Hz, 1H), 4.07 (dd, J=5, 9 Hz, 1H), 4.70 (m, 1H), 5.45 (t, J=12 Hz, 2H), 5.63 (m, 1H); MS(DCI/NH3) m/e 257 (M+H+); Analysis calc'd for $C_{13}H_{24}N_2O_3 \cdot 0.10\ CH_2Cl_2$: C, 59.41, H, 9.21, N, 10.57; found C, 59.27, H, 9.30, N, 10.67.

Step 1i. 3-(1,1-Dimethylethyl)-(S)-4-(3-N$^G$-nitroguanidinopropen-1,Z-yl)-2,2-dimethyl-3-oxazolidinecarboxylate To a solution of the allylic amine of Example 1h (1.0 eq) in EtOH/water 1/1 was added N-nitro-S-methylthiopseudourea (1.2 eq) and TEA (1.2 eq). The reaction was stirred for 3 hr before completion. The reaction was filtered and washed with cold $CH_3OH$. The solid was recrystallized from cold $CH_3OH$, (2×). The product was a white solid obtained in 87% yield: $R_F$ 0.30 ($CH_2Cl_2$/ EtOH/NH$_4$OH 95/5/1); $[\alpha]_D^{20°}=+86.07°$ (c=0.675, $CH_2Cl_2$) $^1$H NMR (300 MHz, CDCl$_3$) δ: 1.45 (s, 9H), 1.50 (s, 3H), 1.59 (s, 3H), 3.70 (dd, J=5, 9 Hz, 1H), 4.05 (m, 1H), 4.10 (m, 1H), 4.40 (m, 1H), 4.64 (m, 1H), 5.50 (m, 2H); $^{13}$C NMR (300 MHz, CDCl$_3$) δ: 24.5, 27.5, 28.5, 38.3, 54.0, 67.5, 81.3, 93.8, 128.75, 130.5, 152.9, 160.0; MS(DCI/NH3) m/e 344 (M+H+); Analysis calc'd for $C_{14}H_{25}N_5O_5$: C, 48.97, H, 7.34, N, 20.40; found C, 48.69, H, 7.54, N, 20.51.

Step 1j. N$^G$-Nitroguanidinyl-4(S)-amino-pent-2,Z-ene-5-ol

To a solution of the protected guanidino compound of Example 1i (1.0 eq) was added a mixture of HCl/HOAc/$H_2O$ 3/1/1 and the reaction was allowed to stir for 3 hr at rt. The reaction volume was diluted (2×) with water and lyophilized. The material was purified on silica gel and eluted with acetonitrile/HOAc/$H_2O$ 3/1/1. The material was a white solid and obtained in 94% yield: $R_F$ 0.30 ($CH_3CN$/HOAc/$H_2O$ 8/1/1); $[\alpha]_D^{20°}=+24.78°$ (c=0.735, $H_2O$). $^1$H NMR (500 MHz, CDCl$_3$) δ: 3.75 (m, 2H), 3.90 (dd, J=9, 15 Hz, 1H), 4.10 (dd, J=9, 15 Hz, 1H), 4.35 (m, 1H), 5.62 (t, J=12 Hz, 1H), 5.95 (m, 1H); $^{13}$C NMR (500 MHz, CDCl$_3$) δ: 41.3, 52.9, 54.4, 127.5, 135.1, 162.1; MS (DCI/NH3) 204.00 (M+H+); Analysis calc'd for $C_6H_{13}N_5O_3 \cdot 3.0$ HCl: C, 21.09; H, 4.95; N, 20.49; found: C, 21.16; H, 5.18; N, 20.47.

EXAMPLE 2

4-Amino-1-N$^G$-nitroguanidino-5-methoxy-(4,S)-2, Z-pentene hydrochloride

Step 2a. 2-Amino-5-phthalimido-(2,S)-3, Z-penten-1-ol hydrochloride

To the product of Example 1g (1.50 g, 3.88 mmol) was added 7.5 mL HOAc, 2.5 mL $H_2O$, and 0.5 mL 12M HCl. The mixture was allowed to stir at ambient temperature for approximately 3 hr, whereupon the volatile components were removed in vacuo to give the title compound as a white solid (1.10 g, 3.88 mmol) in quantitative yield. $^1$H NMR (300 MHz, DMSO-d6) δ: 3.52 (m, 1H), 3.63 (m, 1H), 4.22 (m, 1H), 4.30 (d, J=7.5 Hz, 2H), 5.49–5.58 (m, 2H), 5.78 (m, 1H), 7.82–7.91 (m, 4H), 8.16 (br s, 2H); MS(CI) m/e 247 (M+H)+.

Step 2b. N$^2$-t-Butyloxycarbonyl-2-amino-5-phthalimido-(2,S)-3, Z-penten-1-ol

The product from Example 2a (501 mg, 1.77 mmol) was dissolved in 10 mL of anhydrous DMF. Di-t-butyl dicarbonate (464 mg, 2.12 mmol) and NMM (214 mg, 2.12 mmol) were added, and the reaction was allowed to stir at rt overnight whereupon the reaction was diluted with EtOAc and saturated aqueous KHSO$_4$. The layers were separated, and the organic layer was washed again with saturated aqueous KHSO$_4$, then with brine, dried with $Na_2SO_4$, filtered and the volatile components were removed in vacuo to give the title compound as a white solid (463 mg, 1.3 mmol) which was carried on without further purification. $^1$H NMR (300 MHz, DMSO-d6) δ: 1.38 (s, 9H), 3.38 (m, 2H, partially obscured), 4.29 (t, J=7.5 Hz, 1H), 4.38 (m, 1H), 4.74 (t, J=6 Hz, 1H), 5.35–5.51 (m, 3H), 6.77 (m, 1H), 7.85 (m, 4H); MS (CI) m/e 364 (M+NH4)+ 347 (M+H)+.

Step 2c. N$^4$-t-Butyloxycarbonyl-4-amino-5-methoxy-1-phthalimido-(4,S)-2, Z-pentene The product of Example 2b (330 mg, 0.95 mmol) was dissolved in 4.75 mL of anhydrous DMF. Calcium sulfate (CaSO$_4$) (646 mg, 4.75 mmol), methyl iodide (649 mg, 4.75 mmol), and freshly prepared silver (I) oxide (220 mg, 0.95 mmol) were added, and the reaction was heated at 40°–45° C. for 72 h whereupon EtOAc was added. The organic layer was then washed twice with saturated aqueous NaHCO$_3$, twice with saturated aqueous KHSO$_4$, once with brine, dried over $Na_2SO_4$, filtered, and the the volatile components removed in vacuo. The resulting clear oil was subjected to silica gel chromatography eluting with hexane:acetone (3:1). The title compound was obtained as a white solid (227 mg, 0.63 mmol) contaminated with approximately 30% of the side product, N⁴-(t-butoxycarbonyl-N-methyl)-4-amino-5-methoxy-1-phthalimido-(4,S)-2, Z-pentene. The mixture was combined with material from a previous reaction and carried on without further purification. Removal of the side-product was effected during purification of the product from example 2d. ¹H NMR (300 MHz, CDCl₃) δ: Mixture of major and minor components: major component-1.45 (s, 9H), 3.38 (s, 3H), 3.47 (dd, J=6, 10.5 Hz, 1H), 3.55 (dd, J=6, 10.5 Hz, 1H), 4.37 (m.1H), 4.57 (m, 1H), 4.82 (m, 1H), 5.02 (m, 1H), 5.60 (m, 2H), 7.70 (dd, J=3, 6 Hz, 2H), 7.85 (dd, J=3, 6 Hz, 2H). Partial Data-minor component 1.5 (s, 9H), 2.82 (s, 3H), 3.39 (s, 3H), 5.55 (m, 1H); MS (Cl) major: m/e 378 (M+NH₄)⁺, 361 (M+H)⁺; minor: 392 (M+NH₄)⁺, 375 (M+H)⁺).

Step 2d. N⁴-t-Butyloxycarbonyl-4-amino-1-N$^G$-nitroguanidino-5-methoxy-(4,S)-2, Z-pentene The products from Example 2c (290 mg, 0.80 mmol) were dissolved in 4 mL of anhydrous CH₃OH and hydrazine hydrate (77 mg, 2.40 mmol) was added. The mixture was stirred at ambient temperature under nitrogen atmosphere overnight whereupon it was refluxed for 2 hr to effect phthaloyl deprotection. The volatile components were removed in vacuo and the resulting tan solids (190 mg) were dissolved in 2 mL of CH₃OH. TEA (97 mg, 0.96 mmol) and N-nitro-S-methylthiopseudourea (130 mg, 0.96 mmol) were added and the mixture was stirred at ambient temperature under N₂ atmosphere overnight, whereupon the crude mixture was placed directly on silica gel, eluting with EtOAc:-hexane:HOAc (30:20:2). Removal of the undesired N-methylated compound (obtained because of the mixture starting materials) was performed, fractions judged to be pure by tlc were pooled and the volatile components were removed in vacuo giving the title compound (89 mg, 0.28 mmol) as a white solid. ¹H NMR (300 MHz, CDCl₃) δ: 1.43 (s, 9H), 3.34–3.40 (m, 4H, includes 3.37, s), 3.45 (dd, J=6, 10.5 Hz, 1H), 3.97 (dd, J=7.5, 18 Hz, 1H), 4.33–4.43 (m, 2H), 5.22 (d, J=7.5 Hz, 1H), 5.48–5.55 (m, 2H), 7.63 (br s, 2H), 8.58 (br s, 1H).); MS(Cl) m/e 335 (M+NH₄)⁺, 318 (M+H)⁺.

Step 2e. 4-Amino-1-N$^G$-nitroguanidino-5-methoxy-(4,S)-2, Z-pentene hydrochloride The product of Example 2d was deprotected as in example 1j. ¹H NMR (300 MHz, DMSO-d6) δ: 3.33 (s, 3H), 3.40–3.52 (m, 2H, partially obscured), 3.85–3.95 (br s, 2H), 4.31 (br s, 1H), 5.47 (t, J=12 Hz, 1H), 5.74 (m, 1H), 7.95–8.08 (br s, 2H), 8.10–8.20 (br s, 3H); MS(FAB⁺) m/e 218 (M+H)⁺; Analysis calc'd for C₇H₁₅N₅O₃.1.3 HCl.0.1 dioxane.0.1 Et₂O: C, 33.36; H, 6.50; N, 24.94; found: C, 33.61; H, 6.60; N, 25.26.

EXAMPLE 3

N⁴-Methyl-4-amino-1-(N$^G$-nitroguanidino)-(4,S)-2,Z-penten-5-ol

Step 3a. N²-t-Butyloxycarbonyl-2-amino-1-t-butyldimethylsilyloxy-5-phthalimido-(2,S)-3,Z-pentene To the product of Example 2b (200 mg, 0.58 mmol) and freshly recrystallized imidazole (chloroform/hexane) dissolved in DMF (1 mL) was added t-butyldimethylsilyl chloride (105 mg, 0.70 mmol). The mixture was heated under a N₂ atmosphere at 35° C. overnight whereupon the mixture was diluted with EtOAc and subjected to aqueous washes and extractive work-up in a manner similar to that described for Example 3c giving the title compound (228 mg, 0.49 mmol) as a clear oil which was carried on without further purification. ¹H NMR (300 MHz, CDCl₃) δ: 0.07 (s, 3H), 0.09 (s, 3H), 0.91 (s, 9H), 1.47 (s, 9H), 3.67 (dd, J=4.5, 10.5 Hz, 1H), 3.83 (dd, J=4.5, 10.5 Hz, 1H), 4.38 (m, 1H), 4.54 (m, 1H), 4.70 (br s, 1H), 4.99 (br s, 1H), 5.50–5.68 (m, 2H), 7.72 (dd, J=3, 6 Hz, 2H), 7.74 (dd, J=3, 6 Hz, 2H); MS(Cl) m/e 478 (m+NH₄)⁺, 461 (m+H)⁺.

Step 3b. N²-Methyl-N²-t-butyloxycarbonyl-2,5-diamino-1-t-butyldimethylsilyloxy-(2,S)-3,Z-pentene To the product of example 3a (200 mg, 0.43 mmol) in 1.8 mL anhydrous THF was added methyl iodide (0.059 mL, 0.95 mmol) and potassium hydride (35% suspension in oil rinsed twice with hexane, 57 mg, 1.4 mmol). The reaction was allowed to stir under a nitrogen atmosphere overnight. The mixture was diluted with EtOAc and poured into ice-cold aqueous KH₂PO₄. The layers were separated and the aqueous phase was further extracted with fresh EtOAc, then the combined organic extracts were dried over Na₂SO₄ and evaporated to afford 218 mg of the crude product, MS (Cl) m/e 475 (M+H⁺). A 205 mg (0.43 mmol) portion was dissolved in absolute EtOH (4 mL) and treated with hydrazine hydrate (0.076 mL, 1.3 mmol). The mixture was stirred overnight at ambient temperature, then at reflux for 2 hr. The mixture was concentrated, diluted with EtOAc, and washed with 5% Na₂CO₃. The aqueous phase was back-extracted with fresh EtOAc, then the combined organic fractions were dried (Na₂SO₄) and conc'd to 160 mg. Chromatography (9:1 CHCl₃/MeOH) afforded 66 mg of the title compound. ¹H-NMR (CDCl₃, 300 MHz) δ: 0.05 (s, 6H), 0.88 (s, 9H), 1.46 (s, 9H), 2.78(s, 3H), 3.41 (m, 2H), 3.50–3.75 (m, 3H), 4.80 (brm, 1H), 5.51 (br m, 1H), 5.81 (br s, 2H). MS(Cl) m/e 345 (M+H⁺).

Step 3c. N⁴-Methyl-4-amino-1-(N$^G$-nitroguanidino)-(4,S)-2,Z-penten-5-ol

A solution of Example 3b (63 mg, 0.18 mmol) and TEA (0.028 mL, 0.2 mmol) in MeOH (2 mL) was treated with N-nitro-S-methylthiopseudourea. After stirring for two days, the mixture was diluted with EtOAc and washed twice with 10% aqueous citric acid, once with H₂O, and once with brine, then dried (Na₂SO₄). The mixture was chromatographed (silica gel, 1:1 EtOAc/hexane) to afford 60 mg of purified product. This material was dissolved in 4N HCl/dioxane (5 mL) and stirred for 3 h, then the solvent was removed and the product was purified by passage through a short pad of silica (CH₃CN/H₂O/HOAc, 12:1:11) to afford product.

EXAMPLE 4

1-N$^G$-(Nitroguanidino)-4-amino-2,Z-butene hydrochloride

Step 4a. 1-N-(t-Butoxycarbonyl)amino-4-methylsulfonyloxy-2,Z-butene 1-(N-t-Butoxycarbonyl)amino-2,Z-buten-4-ol (1.3 g, 7.4 mmol) was dissolved in 75 ml dry CH₂Cl₂, 2 mL TEA and cooled to 0° C. MsCl (840 mg, 7.5 mmol) was added to the reaction mixture and stirred for 2 h. The reaction mixture was poured onto a ice/H₂O and extracted with Et₂O (3×50 mL). The combined organic layer was dried and evaporated in vacuo yield crude product. The mesylate product was used for the next reaction without further purification.

Step 4b. 1-N-(t-Butoxycarbonyl)amino-4-phthalimido-2,Z-butene

The product of example 4a was dissolved in 100 mL of dry DMF and 1.3 g of potassium phathalic amide was added in one portion. The reaction mixture was stirred for 24 h and was poured onto a ice/H$_2$). The solution was extracted with EtOAc (3×70 mL), dried and evaporated in vacuo gave an oily residue. These crude product was purified by column chromatography by (EtOAc:hexane 1:3) and gave 1.68 g of product. (24% yield). $^1$H NMR (300 MHz, CD$_3$OD) δ: 1.45 (s, 9H), 3.8–3.9 (m, 2H), 4.25–4.35 (m, 2H), 5.4–5.6 (m, 2H), 7.7–7.8 (m, 4H).

Step 4c. 4-Amino-1-N-(t-butoxycarbonyl)amino-2,Z-butene

To a solution of product from example 4b (1.60 g, 5.2 mmol) in 50 MeOH and N$_2$H$_4$ (2 mL, 85% in H$_2$O) was added. The reaction mixture was refluxed for 24 h and filtered through celite. The solvent was removed in vacuo and the crude product was purified through column chromatography (MeOH:CH$_2$Cl$_2$ 1:9) Rf=0.4 and gave pure product, 720 mg (79%). $^1$H NMR (300 MHz, CD$_3$OD) δ: 1.4 (s, 9H), 3.68–3.7 (m, 2H), 3.3–3.4 (m, 2H), 5.4–5.6 (m, 2H).

Step 4d. 1-N$^G$-(Nitroguanidino)-4-N$^4$-(t-butoxycarbonyl)amino-2,Z-butene

The product of example 4c (500 mg, 2.9 mmol) was dissolved in 20 mL of EtOH/H$_2$O (1:1), 0.2 g TEA and N-nitro-S-methylthiopseudourea (390 mg, 2.2 mmol). The reaction mixture was stirred at r.t. and monitored by tlc (dispearance of starting material). After 3 hr the reaction was complete and the solvent was evaporated in vacuo to yield crude product, 470 mg. This crude material was used without further purification for next step.

Step 4e. 1-N$^G$-(Nitroguanidino)-4-amino-2,Z-butene hydrochloride

The product of Example 4d (470 mg) was dissolved in 5 mL 4N HCl in dioxane and stirred for 4 h at rt. The solvent was removed in vacuo and the residue was washed with MeOH, EtOAc and to yield 321 mg as a light yellow powder. The crude product was purified through column chromatography (CH$_3$CN:AcOH-90:10) and the pure product was further washed with 4N MeOH—HCl and to give pure product, 248 mg (41%). $^1$H NMR (300 MHz, D$_2$O) δ: 3.7–3.8 (m, 2H), 3.9–4.0 (m, 2H), 5.7–5.9 (m, 2H); $^{13}$C NMR (75 MHz, D$_2$O) δ: 161.78, 134.03, 126.61, 40.95, 38.90; MS (DCI/NH3) calc'd for: m/e 174.0991, found 174.0993; 174 (38), 112 (100), 84 (50).

EXAMPLE 5

N$^G$-Nitroguanidinyl-4(R)-amino-pent-2,Z-ene-5-ol

Step 5a. N-[(1,1-Dimethylethoxy)carbonyl]-S-Serine methyl ester

To a solution of L-Boc-serine (0.16 mol) in 150 mL DMF cooled to 0° C. and treated with K$_2$CO$_3$ (0.16 mol) and MeI (0.32 mol). After 30 min, the reaction was warmed to room temperature. After 3 hrs, the reaction was partitioned between H$_2$O and EtOAc, and the EtOAc layer was further washed with brine and added over MgSO$_4$ to yield 0.15 mol, 93%. R$_F$ 0.5 (EtOAc:hexane 1:1); $^1$H NMR (300 MHz, CDCl$_3$) δ: 1.47 (s, 9H), 3.78 (s, 3H), 3.85–3.98 (m, 2H), 4.36 (bs, H), 5.54 (bd, J=5 Hz, 1H); MS(DCI) m/e 220 (m+H)$^+$, 237 (m+NH$_4$)$^+$, 181, 163.

Step 5b. 3-(1,1-Dimethylethyl) 4-methyl-(S)-2,2-dimethyl-3,4-oxazolidinecarboxylate To a solution of the methyl ester of Example 5a (23 mmol) in 150 mL CH$_3$CN was added 2,2-dimethoxypropane (2 eq) and p-toluene sulfonic acid (0.1 eq), and the reaction was heated to reflux and gently distilled for 4 hrs. The solvent was evaporated and the residue was mixed with sat. NaHCO$_3$ and extracted with Et$_2$O. The Et$_2$O extracts were washed with brine and dried over MgSO$_4$ and concentrated in vacuo. Purification was by vacuum distillation at 130° C. and 0.4 mm Hg. R$_F$ 0.2 (2:1 hexane:EtOAc); $^1$H NMR (300 MHz, CDCl$_3$) δ: 1.42 (s, 5H), 1.50 (s, 5H), 1.53 (s, 2H), 1.63 (s, 1H), 1.67 (s, 2H), 3.77 (s, 3H), 4.02–4.08 (m, 1H), 4.12–4.18 (m, 1H), 4.38 (dd, J=3,7 Hz, 0.6H), 4.99 (dd, J=3.7 Hz, 0.4H); MS(DCI) m/e 260 (m+H)$^+$, 277 (m+NH$_4$)$^+$, 221 (m-C$_4$H$_9$).

Step 5c. 1,1-Dimethylethyl (S)-4-formyl-2,2-dimethyl-3-oxazolidinecarboxylate

To a solution of the methyl ester of Example 5b (37 mmol) in 200 mL toluene cooled to −78° C. was added 1M DIBAL (65 mmol, in toluene) over a 15–20 minute period. The reaction was stirred for 3–4 hr at −78° C. and then quenched with CH$_3$OH (12 mL) at −78° C. The reaction was poured into Rochelle salt (1M), extracted with EtOAc and the combined organic extracts were washed with H$_2$O and brine, dried over MgSO$_4$ and concentrated in vacuo. The product distilled in vacuo bp 80°–1° C. (0.7 mm Hg) as a colorless liquid (80%). R$_F$ 0.45 (1:1 EtOAc:hexane); $^1$H NMR (300 MHz, CDCl$_3$) δ: 1.49 (s, 9H), 1.52 (s, 3H), 1.58 (s, 3H), 3.80 (m, 1H), 4.20 (m, 2H), 4.40 (m, 1H), 9.53 (br s, 1H); MS (DCI) 230 (m+H)$^+$, 247 (m+NH$_4$)$^+$, 191 (m-C$_4$H$_9$).

Step 5d. 3-(1,1-Dimethylethyl)-(R)-4-(3-(methoxypropen-2,Z-oyl))-2,2-dimethyl 3-oxazolidinecarboxylate To a solution of the aldehyde of Example 5c (28.4 mmol), which was freshly prepared, in THF at rt was added bis-(2,2,2-trifluoroethyl)methoxycarbonylmethyl)-phosphonate (1.5 eq) as in example 1d. The reaction was stirred at ambient temperature for 4–6 hr and then concentrated in vacuo. Purification by flash chromatography eluting with hexane-EtOAc afforded the title compound as a colorless crystalline solid (91%). mp=52°–4° C.; C; R$_F$0.6 (1:1 EtOAc:hexane); $^1$H NMR (300 MHz, CDCl$_3$) δ: 1.40 (s, 3H), 1.48 (s, 9H), 1.53 (s, 3H), 1.62 (s, 3H), 3.80 (dd, 1H), 4.27 (m, 1H), 5.38 (t, 1H), 5.85 (d, 1H), 6.27 (m, 1H); MS(DCI) m/e 286 (m+H)$^+$, 303 (m+NH$_4$)$^+$, 247, 230. Analysis calc'd for C$_{14}$H$_{23}$NO$_5$.H$_2$O: C, 58.20; H, 8.16; N, 4.85; Found: C, 58.35; H, 8.11; N, 4.78.

Step 5e. 3(1,1-Dimethylethyl)-(R)-4-(3-hydroxypropen-1,Z-yl)-2,2-dimethyl-3-oxazolidinecarboxylate To a solution of the ester from Example 5d (25 mmol) in anhydrous toluene cooled to −78° C. was added DIBAL (5 eq) over a 30 minute period. The reaction was stirred at −78° C. for 3 hr while following by tlc and then quenched at −78° C. with CH$_3$OH. The product was extracted with EtOAc and the combined organic extracts washed with NaOH, H$_2$O and brine, dried over MgSO$_4$ and concentrated in vacuo. Purification by flash chromatography with hexane/EtOAc (1:1) afforded the product as a colorless oil 24 mmol (98%). R$_F$0.30 (1:1 EtOAc:hexane); [α]$_D^{20°}$ = +33.5° (c=0.82, CH$_2$Cl$_2$) $^1$H NMR (300 MHz, CDCl$_3$) δ: 1.47 (s, 9H), 1.49 (s, 3H), 1.56 (s, 3H), 3.70 (dd, 1H), 4.05 (m, 2H), 4.45 (dt, 1H), 4.95 (m, 1H), 5.54 (t, 1H), 5.87 (m, 1H); MS(DCI) m/e 258 (m+H)$^+$, 275 (m+NH$_4$)$^+$, 219 (m-C$_4$H$_9$).

Step 5f. 3-(1,1-Dimethylethyl)-(R)-4-(3-mesyloxypropen-1,Z-yl)-2,2-dimethyl, 3-oxazolidinecarboxylate To a solution of the alcohol from Example 5e (23 mmol) in CH$_2$Cl$_2$ at 0° C. was added TEA (2 eq) and mesyl chloride (1.5 eq). The reaction was stirred at 0° C. for 30 minutes and then extracted with $CH_2Cl_2$. The combined organic extracts were washed with cold $H_2O$, dried over $MgSO_4$ and concentrated in vacuo. The product was provided in quantatative yield and used directly. $R_F$ 0.65 (1:1 EtOAc:hexane); $^1H$ NMR (300 MHz, $CDCl_3$) δ: 5.64–5.77 (m 2H), 4.87–5.10 (m, 2H), 4.62–4.70 (m, 1H), 4.09 (dd, J=7, 8 Hz, 1H), 3.71 (dd, J=3, 8 Hz, 1H), 3.03 (m, 3H), 1.68 (s, 3H), 1.51 (s, 3H), 1.45 (s, 9H); MS(DCI) m/e 336 (m+H)+, 353 (m+$NH_4$)+.

Step 5g. 3-(1,1-Dimethylethyl)-(R)-4-(3-phthalamidopropen-1,Z-yl)-2,2-dimethyl-3-oxazolidinecarboxylate To a solution of the mesylate from Example 5f in anhydrous DMF (1.0M) under a $N_2$ atmosphere at rt was added potassium phthalimide and the reaction was heated at 80° C. for 30 min. The reaction was poured into EtOAc and washed with $H_2O$, brine and dried over $Na_2SO_4$. The organic layer was concentrated in vacuo. The material was purified on silica and eluted with EtOAc/hexane 1/1. The material was a white solid and was obtained in 83%. $R_F$ 0.80, (EtOAc/hexane 5/1); $^1H$ NMR (300 MHz, $CDCl_3$) δ: 1.48 (s, 9H), 1.55 (s, 3H), 1.61 (s, 3H), 3.70 (dd, 1H), 4.22 (t, 2H), 4.60 (m, 1H), 5.00 (m, 1H), 5.63 (m, 1H), 7.71 (dd, 2H), 7.85 (dd, 2H); MS (DCI/$NH_3$) m/e 387 (M+H+), 404 (M+$NH_{4+}$), 331, 287.

Step 5h. 3-(1,1-Dimethylethyl)-(R)-4-(3-aminopropen-1,Z-yl)-2,2-dimethyl-3-oxazolidinecarboxylate To a solution of the phthalimide from Example 4.2 g (10.9 mmol) in $CH_3OH$ under a $N_2$ atmosphere was added hydrazine (11 mmol) and the reaction was stirred and heated to reflux for 1 hr. The reaction was cooled to rt and poured into EtOAc, washed with $H_2O$, brine and dried over $Na_2SO_4$. The product was a slight yellow oil and was obtained in 65.5% yield, 1.82 g (7.1 mmol). $R_F$ 0.80 (EtOAc/PAW 1/1); $[α]_D^{23°}$ = +69.0° (c=0.78, MeOH). $^1H$ NMR (300 MHz, $CDCl_3$) δ: 1.48 (s, 9H), 1.50 (s, 3H), 1.58 (s, 3H), 3.28 (m, 1H), 3.67 (dd, 1H), 4.07 (dd, 1H), 4.70 (m, 1H), 5.45 (t, 2H), 5.63 (m, 1H); MS (DCI-$NH_3$) m/e 257 (M+H+).

Step 5i. 3-(1,1-Dimethylethyl)-(R)-4-(3-$N^G$-nitroguanidinopropen-1,Z-yl)-2,2-dimethyl-3-oxazolidinecarboxylate To a solution of the amine from Example 5h (513 mg, 2.0 mmol) in EtOH/$H_2O$ (1:1) was added the N-nitro-S-methylthiopseudourea (2 eq) and TEA (1.1 eq). The reaction was stirred at rt for 48 hr and then concentrated in vacuo. Purification by flash chromatography eluting with EtOH:$H_2O$ (2:1) afforded the title compound as a white solid (480 mg, 70%). mp=190° C. (decomp); $R_F$ 0.3 (EtOAc-PAW, 1:1); $[α]_D^{23°}$ = +0.90 (c=0.78, MeOH); $[α]_D^{23°}$ = −83.0° (c=1.62, $CH_2Cl_2$). $^1H$ NMR (300 MHz, $CDCl_3$) δ: 1.45 (s, 9H), 1.50 (s, 3H), 1.59 (s, 3H), 3.70 (dd, 1H), 4.05 (m, 1H), 4.10 (m, 1H), 4.40 (m, 1H), 4.64 (m, 1H), 5.50 (m, 2H); $^{13}C$ NMR (300 MHz, $CDCl_3$) δ: 24.5, 27.5, 28.5, 38.3, 54.0, 67.5, 81.3, 93.8, 128.75, 130.5, 152.9, 160.0; MS(DCI) m/e 344 (m+H)+, 299, 244 (m-Boc+H)+; Analysis calc'd for $C_{14}H_{25}N_5O_5$: C, 48.97; H, 7.34; N, 20.40. Found: C, 48.74; H, 7.72; N, 20.22.

Step 5j. $N^G$-Nitroguanidinyl-4(R)-amino-pent-2,Z-ene-5ol

The protected nitroguanidine from Example 5i was deprotected as in Example 1j to provide the product as a white solid (255 mg, 100%). $R_F$ 0.30 (1:1 EtOAc:PAW); $[α]_D^{23°}$ = −25.1° (c=0.45, $H_2O$, pH 6.0). $^1H$ NMR (300 MHz, $D_2O$) δ: 3.68–3.82 (m, 2H), 3.87–4.02 (m, 1H), 4.05–4.13 (m, 1H), 4.31–4.40 (m, 1H), 5.63 (t, 1H), 5.88–5.98 (m, 1H); $^{13}C$ NMR (300 MHz, $D_2O$) δ: 26.1, 41.2, 52.6, 64.2, 99.2, 127.5, 135.0, 161.7; MS (DCI) 204 (m+H)+. Analysis calc'd for $C_6H_{13}N_5O_3$.2.4 HCl 1.1 HOAc: C 27.61; H 5.59; N 19.63. Found: C 27.81; H 5.15; N 19.57. Enantiomeric purity determinations for products from Example 1 and Example 5 were performed by chiral HPLC using a Daicel Crownpak CR(+) 4.6×150 mm column and 0.01M perchloric acid mobile phase at 5° C. with the results: Example 1, 95.6% ee; Example 5, 93.6% ee.

EXAMPLE 6

$N^G$-Aminoguanidino-4(S)-amino-pent-2,Z-ene-5-ol

Step 6a. 3-(1,1-Dimethylethyl)-(S)-4-(3-$N^G$-aminoguanidinopropen-1,Z-yl)-2,2-dimethyl-3-oxazolidinecarboxylate The product of Example 1h (163 mg, 0.64 mmol) was dissolved in 20 mL $Et_2O$ and treated with TEA (178 μL, 1.28) followed by cyanogen bromide (200 μL, 0.60 mmol, 3M in $CH_2Cl_2$) added dropwise over 2 min. After 1 hr, the crude reaction mixture was chromatographed on silica gel eluted with 2:1 hexane-EtOAc to provide 150 mg, 0.53 mmol, 83% yield of the intermediate cyanamide material. The cyanamide (145 mg, 0.52 mmol) was dissolved in 20 mL EtOH and treated with hydrazine monohydrochloride (110 mg, 1.7 mmol) at reflux temperature overnight. The reaction was cooled and the residue from solvent evaporation was chromatographed on silica gel and eluted with 20:1:1 $CH_3CN$—HOAc-$H_2O$ to provide product 147 mg, 0.42 mmol, 70%. $R_F$ 0.4 (5:3 EtOAc-PAW); $^1H$ NMR (300 MHz, $CDCl_3$) δ: 1.47 (s, 9H), 1.50 (s, 3H), 1.57 (s, 3H), 2.00 (s, 3H), 3.70 (dd, J=2, 7 Hz, 2H), 3.78 (bs, 1H), 4.06 (dd, J=6, 8 Hz, 1H), 4.20–4.40 (bs, 1H), 4.56–4.62 (m, 1H), 5.42–5.56 (m, 2H); MS(DCI/$NH_3$) m/e 314(m+H)+, 284, 257.

Step 6b. $N^G$-Aminoguanidino-4(S)-amino-pent-2,Z-ene-5-ol

The protected product of Example 6a (75 mg, 0.21 mmol) was treated with 1 mL 6N HCl for 3 hr at ambient temperature. The crude reaction was diluted with $H_2O$ and lyophilized to provide 58.6 mg, 0.20 mmol, 95% yield (as 5.75 HCl salt); HPLC: 99.1% pure (YMC-ODS-AQ column, elution with $H_2O$). $R_F$ 0.2 (1:2 EtOAc-PAW); $^1H$ NMR (300 MHz, $D_2O$) δ: 3.68–3.81 (m, 2H), 3.99–4.03 (m, 2H), 4.22–4.29 (m, 1H), 5.66 (tt, J=1, 7 Hz, 1H), 5.89–5.97 (m, 1H); MS (DCI/$NH_3$) 174(M+H)+; $[α]_D^{23°}$ = +9.5° (c=2.1, $H_2O$); Anal calc'd for $C_6H_{15}N_5O$.5.75 HCl: C, 18.82; H, 5.46; N, 18.29; found: C, 19.12; H, 4.63; N, 17.68.

EXAMPLE 7

$N^G$-Methylguanidinyl-4(S)-amino-pent-2,Z-ene-5-ol

Step 7a. 3-(1,1-Dimethylethyl)-(S)-4-(3-$N^G$-methyliguanidinopropen-1,Z-yl)-2,2-dimethyl-3-oxazolidinecarboxylate To a solution of the allylic amine from Example 1h in EtOH/$H_2O$ 1/1 (2 mL) was added N,S-dimethylpseudothiouronium hydroiodide and TEA and the reaction was stirred at rt for 16 hr. The reaction was concentrated in vacuo. The material was purified on silica gel and eluted with 12/1/1 $CH_3CN$/HOAc/$H_2O$. The resulting material was a colorless oil and obtained in 81% yield. $R_F$ 0.30 ($CH_3CN$/HOAc/$H_2O$ 12/1/1); $^1H$ NMR (300 MHz, $CD_3OD$) δ: 1.48 (s, 9H), 1.52 (s, 3H), 1.58 (s, 3H), 1.93 (s, 3H), 3.68 (dd, J=9, 12 Hz, 1H), 3.72 (m, 1H), 4.12 (dd, J=9, 12 Hz, 1H), 4.25 (m, 1H), 4.70 (m, 1H), 5.55 (m, 2H); MS(DCI/NH3) m/e 313 (M+H+); $[\alpha]_D^{20°} = +80.61°$ (c=0.962, CH2Cl2); Analysis calc'd for $C_{15}H_{28}N_4O_3 \cdot 2.0$ HOAc $\cdot 0.9$ H2O: C, 50.85, H, 8.49, N, 12.48; Found: C, 50.63; H, 8.12; N, 12.65.

Step 7b. $N^G$-Methylguanidinyl-4(S)-amino-pent-2,Z-ene-5-ol

To a solution of the protected guanidine of example 7a (1.0 eq) in 66% HOAc (10 mL) was added HCl (2.0 eq) and the reaction was stirred at rt for 1 hr. The solvent was removed in vacuo. The material was purified on silica gel and eluted with CH3CN/HOAC/H2O 6/1/1. The material was a white solid and obtained in 81% yield. $R_F$ 0.20 (CH3CN/HOAc/H2O 6/1/1); 1H NMR (300 MHz, D2O) δ: 2.85 (s, 3H), 3.74 (m, 2H), 4.00 (dd, J=7, 12 Hz, 1H), 4.25 (m, 2H), 5.65 (tt, J=7, 11 Hz, 1H), 5.93 (m, 1H); MS(DCI/NH3) m/e 173 (M+H+); $[\alpha]_D^{20°} = +18.72°$ (c=0.561, H2O); Analysis calc'd for $C_7H_{16}N_4O \cdot 2.9$ HCl: C, 30.25, H, 6.85, N, 20.16; Found C, 30.37, H, 6.70, N, 19.84.

The foregoing examples are merely illustrative of the invention and are not intended to limit the invention to the disclosed compounds. Variations and changes which are obvious to one skilled in the art are intended to be within the scope and nature of the invention which is defined in the appended claims.

What is claimed is:

1. A compound of the formula:

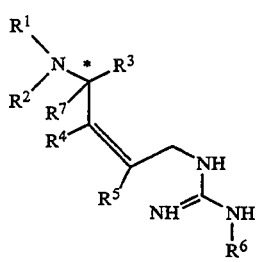

or a pharmaceutically-acceptable salt, ester, amide or prodrug thereof, wherein $R^1$ is selected from the group consisting of
(1) hydrogen;
(2) $C_1-C_6$-alkyl;
(3) $C_6-C_{12}$-aryl;
(4) substituted $C_6-C_{12}$-aryl;
(5) $C_6-C_{12}$-aryl-$C_1-C_4$-alkyl;
(6) substituted $C_6-C_{12}$-aryl-$C_1-C_4$-alkyl;
(7) $C_2-C_6$-alkenyl; and
(8) N-protecting group;

$R^2$ is hydrogen;

$R^3$ is
CH(OH)—$R^8$, wherein $R^8$ is hydrogen, $C_1-C_6$-alkyl, or $C_6-C_{12}$-aryl; or
CH(OR$^9$)—$R^8$, wherein $R^8$ is defined as above, and $R^9$ is $C_1-C_6$-alkyl or a hydroxy protecting group;

$R^4$ is hydrogen or $C_1-C_4$-alkyl;
$R^5$ is hydrogen, $C_1-C_4$-alkyl or halogen:
$R^6$ is selected from the group consisting of:
(1) hydrogen;
(2) $C_1-C_6$-alkyl;
(3) $C_6-C_{12}$-aryl-$C_1-C_6$-alkyl;
(4) cyano;
(5) nitro;
(6) hydroxy;
(7) amino;
(8) —OR$^{10}$, wherein $R^{10}$ is a hydroxy protecting group; and
(9) —NHR$^{11}$, wherein $R^{11}$ is a N-protecting group;
$R_7$ is hydrogen or $C_1-C_4$alkyl; and *may be a chiral center.

2. A compound according to claim 1, wherein $R^1$, $R^2$, $R^4$, $R^5$, $R^6$, and $R^7$ are as defined above and $R^3$ is CH2OH.

3. A compound according to claim 1, wherein $R^1$, $R^2$, $R^4$, $R^5$, and $R^7$ are hydrogen, $R^6$ is nitro, and $R^3$ is CH2OH.

4. A compound according to claim 1, which is: $N^G$-Nitroguanidinyl-4(S)-amino-pent-2,Z-ene-5ol; 4-Amino-1-$N^G$-nitroguanidino-5-methoxy-(4,S)-2, Z-pentene; $N^4$-Methyl-4-amino-1-($N^G$-nitroguanidino)-(4,S)-2,Z-penten-5-ol; $N^G$-Nitroguanidinyl-4(R)-amino-pent-2,Z-ene-5-ol; $N^G$-Aminoganidino-4(S)-amino-pent-2,Z-ene-5-ol; or $N^G$-Methylguanidinyl-4(S)-amino-pent-2,Z-ene-5-ol.

5. A compound according to claim 4, which is: $N^G$-Nitroguandinyl-4(S)-amino-pent-2,Z-ene-5-ol; $N^G$-Nitroguanidinyl-4(R)-amino-pent-2,Z-ene-5-ol; or $N^G$-Aminoguanidino-4(S)-amino-pent-2,Z-ene-5-ol.

6. A pharmaceutical composition for treating disorders of the vascular system or diseases of the cartilage characterized by the regulation of soluble guanylate cyclase or nitric oxide synthase activity, comprising a pharamaceutically-acceptable carrier and a therapeutically-effective amount of a compound according to claim 1.

* * * * *